United States Patent [19]

Howe et al.

[11] 4,199,506

[45] Apr. 22, 1980

[54] 2,4-DISUBSTITUTED-5-THIAZOLECAR-BOXYLIC ACIDS AND DERIVATIVES

[75] Inventors: Robert K. Howe, Bridgeton; Len F. Lee, Maryland Heights, both of Mo.

[73] Assignee: Monsanto Company, St. Louis, Mo.

[21] Appl. No.: 906,183

[22] Filed: May 15, 1978

[51] Int. Cl.$^2$ .................. A01W 9/02; A01N 9/12; C07D 277/34

[52] U.S. Cl. ..................... 548/201; 71/90; 71/118; 548/200; 548/188

[58] Field of Search ................... 260/302 R

[56] References Cited

U.S. PATENT DOCUMENTS

| | | | |
|---|---|---|---|
| 2,961,446 | 11/1960 | Harman et al. | 260/302 R |
| 3,155,678 | 11/1964 | Hatchard | 260/302 R |
| 3,700,677 | 10/1972 | Cleménce et al. | 260/302 R |
| 3,725,427 | 4/1973 | Harrison et al. | 260/302 R |
| 3,876,652 | 4/1975 | Pittet et al. | 260/302 R |
| 3,882,110 | 5/1975 | Cleménce | 260/302 R |
| 3,957,808 | 5/1976 | Miller et al. | 260/302 A |

FOREIGN PATENT DOCUMENTS

| | | |
|---|---|---|
| 658353 | 3/1938 | Fed. Rep. of Germany . |
| 1187620 | 2/1965 | Fed. Rep. of Germany . |

OTHER PUBLICATIONS

Clark et al., "Journal of the Chem. Soc.", (B), 1966, pp. 339, 341–343.
Wohmann, "Chemisches Zentralblatt", 1891, pp. 68–69.
"Chemical Abstracts", vol. 40, col. 4059–4061.

*Primary Examiner*—Glennon H. Hollrah
*Assistant Examiner*—James H. Turnipseed
*Attorney, Agent, or Firm*—Richard H. Shear; Donald W. Peterson

[57] ABSTRACT

2,4-Disubstituted-5-thiazolecarboxylic acids and derivatives thereof have been found to reduce herbicidal injury of corn, rice and sorghum plants due to the application thereto of acetamide herbicides.

28 Claims, No Drawings

2,4-DISUBSTITUTED-5-THIAZOLECARBOXYLIC ACIDS AND DERIVATIVES

This invention relates to novel 2,4-disubstituted-5-thiazolecarboxylic acids and derivatives thereof as well as their use in compositions and methods for reducing herbicidal injury. More specifically, the invention relates to novel compositions and methods for reducing injury to crop plants by herbicides, such as acetamides, especially acetanilides, which comprises treating the crop plant locus or the seed of the crop plant with an effective amount of a 2,4-disubstituted-5-thiazolecarboxylic acid or derivative thereof that will be described more fully below.

BACKGROUND OF THE INVENTION

Acetamide herbicides are very useful for controlling certain weeds, especially grasses, in the presence of growing crops. However, many of the acetamide herbicides injure certain crop plants slowing growth and development at application rates necessary to stunt or kill the weeds. Accordingly, some of the acetamide herbicides cannot be used for controlling weeds in the presence of certain crops. Obviously, a safening agent consisting of a composition that could be used to treat the seed of the crop plant, the crop plant locus or the crop plant itself, resulting in a reduction of injury due to application of the herbicide without a corresponding reduction of herbicidal action on the weed, would be quite beneficial.

DESCRIPTION OF THE INVENTION

In accordance with the novel aspects of the present invention, injury to crop plants, such as corn, rice and sorghum, due to application thereto of acetamide, herbicides, especially acetanilide herbicides such as 2-chloro-2',6'-diethyl-N-(methoxymethyl)acetanilide (hereinafter referred to by its common name, alachlor), 2-chloro-2',6'-diethyl-N-(butoxymethyl)acetanilide (hereinafter referred to by its common name, butachlor), 2-chloro-N-isopropylacetanilide (hereinafter referred to by its common mane, propachlor), N-(ethoxymethyl)-N-(2-ethyl-6-methyl-1-cyclohexen-1-yl)-2-chloroacetamide, N-(ethoxymethyl)-N-(2,5-dimethyl-1-cyclopenten-1-yl)-2-chloroacetamide, 2-chloro-N-(2-methoxy-1-methylethyl)-6'-ethyl-o-acetotoluidide and 2-chloro-N-(ethoxymethyl)-6'-ethyl-o-acetotoluidide, may be reduced without a corresponding reduction in injury to the weeds by application to the crop plant locus or the seed of the crop plant prior to planting of an effective amount of a safening agent comprising a 2,4-disubstituted-5-thiazolecarboxylic acid or derivative thereof having the formula

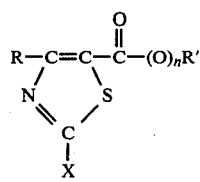

wherein n is zero or one; X is selected from the group consisting of chloro, bromo, iodo, lower alkoxy, phenoxy and phenoxy substituted by one or two groups independently selected from the group consisting of lower alkyl and halogen; R is selected from the group consisting of alkyl having up to nine carbon atoms, haloalkyl and trialkoxymethyl; when n is one, R' is selected from the group consisting of hydrogen, agriculturally acceptable cations, alkyl (1–10 carbon atoms being preferred), lower alkenyl, lower alkynyl, lower alkoxy lower alkyl, haloalkyl, benzyl, phenyl and phenyl substituted by one or two members selected from the group consisting of halogen, lower alkyl, trifluoromethyl and nitro; when n is zero, R' is selected from the group consisting of chloro, amino and mono- or dilower alkylamino.

All of the compounds of the above formula are believed to be novel except those in which R is alkyl.

As used herein, the terms "lower alkyl", lower alkoxy "lower alkenyl" and "lower alkynyl" are understood to include alkyl, alkenyl and alkynyl groups having up to five carbon atoms, inclusive.

The terms "alkyl", "alkenyl" and "alkynyl" are understood to include branched and unbranched groups. When R' is lower alkenyl, allyl is preferred. When R' is lower alkynyl, propargyl is preferred.

The term "haloalkyl" is understood to mean those alkyl moieties having up to five carbon atoms wherein at least one hydrogen atom has been replaced by a halogen atom. Specifically included are those alkyl moieties in which all of the hydrogen atoms have been replaced by halogen atoms, such as trifluoromethyl.

The term "agriculturally acceptable cations" is understood to mean those cations that are commonly used to form the salt of the free acid. Such cations include, but are not limited to, alkali metal, alkaline earth, substituted amine and ammonium cations.

The amount of safening agent employed in the method and compositions of the invention will vary depending upon the particular herbicide with which the agent is employed, the rate of application of the herbicide, the crop to be protected as well as the manner of application of the safening agent. In each instance, the amount employed is a safening effective amount, i.e., the amount which reduces crop injury by the acetamide herbicide.

The safening agent may be applied to the plant locus in a mixture with the herbicide sequentially or it may be applied directly to the seed of the crop plant. By application to the "plant locus" is meant application to the plant growing medium, such as the soil, as well as the seeds, emerging seedlings, roots, stems, leaves, flowers, fruits or other plant parts.

The amount of herbicide employed is well within the skill of the art and is disclosed in various patents. Propachlor and its herbicidal use is disclosed in U.S. Pat. No. 2,863,752 and No. Reissue 26,961. Alachlor, butachlor and 2-chloro-N-(ethoxymethyl)-6'-ethyl-o-acetotoluidide and their herbicidal use are disclosed in U.S. Pat. Nos. 3,442,945 and 3,547,620. U.S. Pat. No. 3,937,730 discloses and claims 2-chloro-N-(2-methoxy-1-methylethyl)-6'-ethyl-o-acetotoluidide. The herbicidal use of N-(ethoxymethyl)-N-(2-ethyl-6-methyl-1-cyclohexen-1-yl)-2-chloroacetamide and N-(ethoxymethyl)-N-(2,5-dimethyl-1-cyclopenten-1-yl)-2-chloroacetamide is disclosed in Application Ser. No. 897,472, filed Apr. 18, 1978 by John P. Chupp now abandoned.

To illustrate the effectiveness of the 2,4-disubstituted-5-thiazolecarboxylic acids and derivatives thereof, the following examples are presented. These examples are presented merely as being illustrative of the novel aspects of the invention and are not intended to be a limitation as to the scope thereof.

EXAMPLE 1

A good grade of top soil is placed in a container and compacted to a depth of approximately 1.27 cm. from the top of said container. A predetermined number of seeds of each of the crop species to be tested are placed on top of the soil. A quantity of soil sufficient to substantially fill the container is measured and placed in a second container. A measured quantity of the safening agent dispersed or dissolved in a suitable carrier is applied to the soil in the second container. A measured quantity of the acetamide herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and acetamide herbicide and the pots are leveled. The pots are then placed on a sand bench in the greenhouse and watered from below as needed. The plants are observed at the end of approximately 21 days and the results in terms of percent inhibition of each seed lot are recorded. For each test series, a pot is also prepared containing no acetamide herbicide and no safening agent as a control. Additionally, for each test, pots are prepared with soil covering the seed containing no acetamide herbicide and only the measured amount of safening agent being incorporated into the soil covering the seeds to ascertain any herbicidal effect of the safening agent alone. For each series of tests, the herbicidal effect of the acetamide herbicide is observed from pots treated with the same quantity of herbicide alone. The "safening effect" is determined by adding the herbicidal effect of the acetamide herbicide when applied alone to the herbicidal effect of the safening agent when applied alone (in no instance, however, will this sum be greater than 100) and substracting from that the herbicidal effect obtained when both the herbicide and safening agent are incorporated into the soil as discussed above.

Table I summarizes the results obtained when the compounds of the invention were tested in accordance with the procedure of Example 1 utilizing alachlor as the herbicide.

Table I

| Safening Agent | Rate of Safening Agent (kg/h) | Rate of Herbicide (kg/h) | Crop | Safening Effect |
|---|---|---|---|---|
| Ethyl 2-chloro-4-isopropyl-5-thiazolecarboxylate | 8.96 | 4.48 | sorghum | 60 |
| | 8.96 | 4.48 | rice | 20 |
| Ethyl 2-chloro-4-ethyl-5-thiazolecarboxylate | 8.96 | 4.48 | sorghum | 64 |
| | 8.96 | 4.48 | rice | 25 |
| Ethyl 2-chloro-4-trifluoromethyl-5-thiazolecarboxylate | 8.96 | 4.48 | sorghum | 65 |
| | 8.96 | 4.48 | rice | * |
| Ethyl 2-chloro-4-t-butyl-5-thiazolecarboxylate | 8.96 | 4.48 | sorghum | 75 |
| | 8.96 | 4.48 | rice | * |
| Butyl 2-chloro-4-trifluoromethyl-5-thiazolecarboxylate | 8.96 | 2.24 | sorghum | 53 |
| | 8.96 | 2.24 | rice | 58 |
| Hexyl 2-chloro-4-trifluoromethyl-5-thiazolecarboxylate | 8.96 | 2.24 | sorghum | 43 |
| | 8.96 | 2.24 | rice | 33 |
| Octyl 2-chloro-4-trifluoromethyl-5-thiazolecarboxyate | 8.96 | 2.24 | sorghum | 38 |
| | 8.96 | 2.24 | rice | 23 |
| Phenyl 2-chloro-4-trifluoromethy-5-thiazolecarboxylate | 8.96 | 2.24 | sorghum | 30 |
| | 8.96 | 2.24 | rice | * |
| p-Chlorophenyl 2-chloro-4-trifluoromethyl-5-thiazolecarboxylate | 8.96 | 2.24 | sorghum | 30 |
| | 8.96 | 2.24 | rice | 20 |
| Ethyl 2-phenoxy-4-trifluoromethyl-5-thiazolecarboxylate | 8.96 | 2.24 | sorghum | 55 |
| | 8.96 | 2.24 | rice | 30 |
| Ethyl 2-ethoxy-4-triethoxymethyl-5-thiazolecarboxylate | 8.96 | 2.24 | sorghum | 55 |
| | 8.96 | 2.24 | rice | 70 |
| Allyl 2-chloro-4-trifluoromethyl-5-thiazolecarboxylate | 8.96 | 2.24 | sorghum | 55 |
| | 8.96 | 2.24 | rice | 70 |
| 2-Chloro-4-trifluoromethyl-5-thiazolecarboxylic acid | 8.96 | 2.24 | sorghum | 70 |
| | 8.96 | | rice | * |
| Methyl 2-chloro-4-trifluoromethyl-5-thiazolecarboxylate | 8.96 | 2.24 | sorghum | 40 |
| | 8.96 | 2.24 | rice | * |
| Isoropyl 2-chloro-4-trifluoromethyl-5-thiazolecarboxylate | 8.96 | 2.24 | sorghum | 75 |
| | 8.96 | 2.24 | rice | * |
| Benzyl 2-chloro-4-trifluoromethyl-5-thiazolecarboxylate | 8.96 | 2.24 | sorghum | 50 |
| | 8.96 | 2.24 | rice | * |
| Butoxyethyl 2-chloro-4-trifluoromethyl-5-thiazolecarboxylate | 8.96 | 2.24 | sorghum | 65 |
| | 8.96 | 2.24 | rice | 28 |
| β-trichloroethyl 2-chloro-4-trifluoromethyl-5-thiazolecarboxylate | 8.96 | 2.24 | sorghum | 70 |
| | 8.96 | 2.24 | rice | * |
| Methyl 2-chloro-4-heptafluoropropyl-5-thiazolecarboxylate | 4.48 | 2.24 | sorghum | 20 |
| | 4.48 | 2.24 | rice | * |
| Ethyl 2-chloro-4-pentafluoroethyl-5-thiazolecarboxylate | 8.96 | 2.24 | sorghum | 55 |
| | 8.96 | 2.24 | rice | 63 |
| Ethyl 2-bromo-4-trifluoromethyl-5-thiazolecarboxylate | 8.96 | 2.24 | sorghum | 40 |
| | 8.96 | 2.24 | rice | 75 |
| Ethyl 2-iodo-4-trifluoromethyl-5-thiazolecarboxylate | 8.96 | 4.48 | sorghum | 40 |
| | 8.96 | 4.48 | rice | 20 |
| 2-Chloro-4-trifluoromethyl-5-thiazolecarboxylic acid chloride | 8.96 | 4.48 | sorghum | 40 |
| | 8.96 | 4.48 | rice | * |
| N,N-diethyl-2-chloro-4-trifluoromethyl-5-thiazolecarboxamide | 8.96 | 4.48 | sorghum | 23 |
| | 8.96 | 4.48 | rice | 25 |
| Ethyl 2-chloro-4-trichloro- | 8.96 | 4.48 | sorghum | * |

Table I-continued

| Safening Agent | Rate of Safening Agent (kg/h) | Rate of Herbicide (kg/h) | Crop | Safening Effect |
|---|---|---|---|---|
| methyl-5-thiazolecarboxylate | 8.96 | 4.48 | rice | 25 |
| Triethanolamine salt of 2-chloro-4-trifluoromethyl-5-thiazolecarboxylic acid | 8.96 | 2.24 | sorghum | 57 |
|  | 8.96 | 2.24 | rice | * |
| Ethyl 2-fluoro-4-trifluoromethyl-5-thiazolecarboxylate | 8.96 | 2.24 | sorghum | * |
|  | 8.96 | 2.24 | rice | * |
| Diethylamine satl of 2-chloro-4-trifluoromethyl-5-thiazolecarboxylic acid | 8.96 | 2.24 | sorghum | 22 |
|  | 8.96 | 2.24 | rice | * |
| Isoropylamine salt of 2-chloro-4-trifluoromethyl-5-thiazolecarboxylic acid | 8.96 | 2.24 | sorghum | 42 |
|  | 8.96 | 2.24 | rice | * |
| Ethyl 2-chloro-4-trifluoromethyl-5-thiazolecarboxylate | 8.96 | 0.56 | sorghum | 93 |
|  | 8.96 | 1.12 | sorghum | 95 |
|  | 8.96 | 2.24 | sorghum | 87 |
|  | 8.96 | 4.48 | sorghum | 75 |
|  | 8.96 | 0.56 | rice | 53 |
|  | 8.96 | 1.12 | rice | 25 |
|  | 8.96 | 2.24 | rice | 25 |
|  | 8.96 | 4.48 | rice | 35 |
| Ethyl 2-chloro-4-isopropyl-5-thiazolecarboxylate | 8.96 | 0.56 | sorghum | 90 |
|  | 8.96 | 1.12 | sorghum | 85 |
|  | 8.96 | 2.24 | sorghum | 70 |
|  | 8.96 | 4.48 | sorghum | 55 |
|  | 8.96 | 0.56 | rice | 65 |
|  | 8.96 | 1.12 | rice | 64 |
|  | 8.96 | 2.24 | rice | * |
|  | 8.96 | 4.48 | rice | 25 |
| Ethyl 2-chloro-4-ethyl-4-thiazolecarboxylate | 8.96 | 0.56 | sorghum | 80 |
|  | 8.96 | 1.12 | sorghum | 58 |
|  | 8.96 | 2.24 | sorghum | 57 |
|  | 8.96 | 4.48 | sorghum | 24 |
|  | 8.96 | 0.56 | rice | 80 |
|  | 8.96 | 1.12 | rice | 84 |
|  | 8.96 | 2.24 | rice | * |
|  | 8.96 | 4.48 | rice | * |
| Ethyl 2-chloro-4-t-butyl-5-thiazolecarboxylate | 8.96 | 0.56 | sorghum | 99 |
|  | 8.96 | 1.12 | sorghum | 89 |
|  | 8.96 | 2.24 | sorghum | 85 |
|  | 8.96 | 4.48 | sorghum | 40 |
|  | 8.96 | 0.56 | rice | 55 |
|  | 8.96 | 1.12 | rice | 30 |
|  | 8.96 | 2.24 | rice | 45 |
|  | 8.96 | 4.48 | rice | * |
| Butyl 2-chloro-4-trifluoromethyl-5-thiazolecarboxylate | 8.96 | 0.56 | sorghum | * |
|  | 8.96 | 1.12 | sorghum | 55 |
|  | 8.96 | 2.24 | sorghum | 55 |
|  | 8.96 | 4.48 | sorghum | 60 |
|  | 8.96 | 0.56 | rice | 38 |
|  | 8.96 | 1.12 | rice | 38 |
|  | 8.96 | 2.24 | rice | * |
|  | 8.96 | 4.48 | rice | * |
| Hexyl 2-chloro-4-trifluoromethyl-5-thiazolecarboxylate | 8.96 | 0.56 | sorghum | * |
|  | 8.96 | 1.12 | sorghum | 45 |
|  | 8.96 | 2.24 | sorghum | 45 |
|  | 8.96 | 4.48 | sorghum | 60 |
|  | 8.96 | 0.56 | rice | 43 |
|  | 8.96 | 1.12 | rice | 40 |
|  | 8.96 | 2.24 | rice | 48 |
|  | 8.96 | 4.48 | rice | * |
| Octyl 2-chloro-4-trifluoromethyl-5-thiazolecarboxylate | 8.96 | 0.56 | sorghum | 45 |
|  | 8.96 | 1.12 | sorghum | 80 |
|  | 8.96 | 2.24 | sorghum | 60 |
|  | 8.96 | 4.48 | sorghum | 55 |
|  | 8.96 | 0.56 | rice | 88 |
|  | 8.96 | 1.12 | rice | 30 |
|  | 8.96 | 2.24 | rice | 38 |
|  | 8.96 | 4.48 | rice | 28 |
| Ethyl 2-phenoxy-4-trifluoromethyl-5-thiazolecarboxylate | 8.96 | 0.56 | sorghum | 25 |
|  | 8.96 | 1.12 | sorghum | 50 |
|  | 8.96 | 2.24 | sorghum | 25 |
|  | 8.96 | 4.48 | sorghum | 45 |
|  | 8.96 | 0.56 | rice | 48 |
|  | 8.96 | 1.12 | rice | 45 |
|  | 8.96 | 2.24 | rice | * |
|  | 8.96 | 4.48 | rice | * |
| Ethyl 2-ethoxy-4-triethoxymethyl-5-thiazolecarboxylate | 8.96 | 0.56 | sorghum | * |
|  | 8.96 | 1.12 | sorghum | 35 |
|  | 8.96 | 2.24 | sorghum | 20 |

Table I-continued

| Safening Agent | Rate of Safening Agent (kg/h) | Rate of Herbicide (kg/h) | Crop | Safening Effect |
|---|---|---|---|---|
| | 8.96 | 4.48 | sorghum | |
| | 8.96 | 0.56 | rice | |
| | 8.96 | 1.12 | rice | * |
| | 8.96 | 2.24 | rice | * |
| | 8.96 | 4.48 | rice | * |
| Allyl 2-chloro-4-trifluoromethyl-5-thiazolecarboxylate | 8.96 | 0.56 | sorghum | 30 |
| | 8.96 | 1.12 | sorghum | 60 |
| | 8.96 | 2.24 | sorghum | 45 |
| | 8.96 | 4.48 | sorghum | 65 |
| | 8.96 | 0.56 | rice | 73 |
| | 8.96 | 1.12 | rice | 20 |
| | 8.96 | 2.24 | rice | 23 |
| | 8.96 | 4.48 | rice | * |
| Phenyl 2-chloro-4-trifluoromethyl-5-thiazolecarboxylate | 8.96 | 0.56 | sorghum | 75 |
| | 8.96 | 1.12 | sorghum | 60 |
| | 8.96 | 2.24 | sorghum | 65 |
| | 8.96 | 4.48 | sorghum | 60 |
| | 8.96 | 0.56 | rice | 58 |
| | 8.96 | 1.12 | rice | 32 |
| | 8.96 | 2.24 | rice | 20 |
| | 8.96 | 4.48 | rice | * |
| p-Chlorophenyl 2-chloro-4-trifluoromethyl-5-thiazolecarboxylate | 8.96 | 0.56 | sorghum | 75 |
| | 8.96 | 1.12 | sorghum | 70 |
| | 8.96 | 2.24 | sorghum | 65 |
| | 8.96 | 4.48 | sorghum | 65 |
| | 8.96 | 0.56 | rice | 43 |
| | 8.96 | 1.12 | rice | 32 |
| | 8.96 | 2.24 | rice | 25 |
| | 8.96 | 4.48 | rice | * |
| Isopropyl 2-chloro-4-trifluoromethyl-5-thiazolecarboxylate | 8.96 | 0.56 | sorghum | 55 |
| | 8.96 | 1.12 | Sorghum | 47 |
| | 8.96 | 2.24 | sorghum | 40 |
| | 8.96 | 4.48 | sorghum | 28 |
| | 8.96 | 0.56 | rice | 75 |
| | 8.96 | 1.12 | rice | 50 |
| | 8.96 | 2.24 | rice | 20 |
| | 8.96 | 4.48 | rice | * |
| $\beta$-trichloroethyl 2-chloro-4-trifluoromethyl-5-thiazolecarboxylate | 8.96 | 0.56 | sorghum | 60 |
| | 8.96 | 1.12 | sorghum | 57 |
| | 8.96 | 2.24 | sorghum | 55 |
| | 8.96 | 4.48 | sorghum | 40 |
| | 8.96 | 0.56 | rice | 50 |
| | 8.96 | 1.12 | rice | 50 |
| | 8.96 | 2.24 | rice | 35 |
| | 8.96 | 4.48 | rice | * |
| Ethyl 2-bromo-4-trifluoromethyl-5-thiazolecarboxylate | 8.96 | 0.56 | sorghum | 73 |
| | 8.96 | 1.12 | sorghum | 70 |
| | 8.96 | 2.24 | sorghum | 65 |
| | 8.96 | 4.48 | sorghum | 65 |
| | 8.96 | 0.56 | rice | 60 |
| | 8.96 | 1.12 | rice | 60 |
| | 8.96 | 2.24 | rice | 45 |
| | 8.96 | 4.48 | rice | 20 |
| Ethyl 2-iodo-4-trifluromethyl-5-thiazolecarboxylate | 8.96 | 0.56 | sorghum | 80 |
| | 8.96 | 1.12 | sorghum | 75 |
| | 8.96 | 2.24 | sorghum | 75 |
| | 8.96 | 4.48 | sorghum | 78 |
| | 8.96 | 0.56 | rice | 34 |
| | 8.96 | 1.12 | rice | 36 |
| | 8.96 | 2.24 | rice | * |
| | 8.96 | 4.48 | rice | 23 |
| 2-Chloro-4-trifluoromethyl-5-thiazolecarboxylic acid chloride | 8.96 | 0.56 | sorghum | 80 |
| | 8.96 | 1.12 | sorghum | 60 |
| | 8.96 | 2.24 | sorghum | * |
| | 8.96 | 4.48 | sorghum | * |
| | 8.96 | 0.56 | rice | * |
| | 8.96 | 1.12 | rice | * |
| | 8.96 | 2.24 | rice | * |
| | 8.96 | 4.48 | rice | * |
| N,N-diethyl-2-chloro-4-trifluoromethyl-5-thiazolecarboxamide | 8.96 | 0.56 | sorghum | 25 |
| | 8.96 | 1.12 | sorghum | * |
| | 8.96 | 2.24 | sorghum | * |
| | 8.96 | 4.48 | sorghum | * |
| | 8.96 | 0.56 | rice | 45 |
| | 8.96 | 1.12 | rice | * |
| | 8.96 | 2.24 | rice | * |
| | 8.96 | 4.48 | rice | * |
| Ethyl 2-chloro-4-trichloromethyl-5-thiazolecarboxylate | 8.96 | 0.56 | sorghum | 45 |
| | 8.96 | 1.12 | sorghum | * |

Table I-continued

| Safening Agent | Rate of Safening Agent (kg/h) | Rate of Herbicide (kg/h) | Crop | Safening Effect |
|---|---|---|---|---|
| | 8.96 | 2.24 | sorghum | * |
| | 8.96 | 4.48 | sorghum | * |
| | 8.96 | 0.56 | rice | 75 |
| | 8.96 | 1.12 | rice | 55 |
| | 8.96 | 2.24 | rice | 45 |
| | 8.96 | 4.48 | rice | 50 |
| Methyl 2-chloro-4-trifluoro-methyl-5-thiazolecarboxylate | 8.96 | 0.56 | sorghum | 80 |
| | 8.96 | 1.12 | sorghum | 75 |
| | 8.96 | 2.24 | sorghum | 70 |
| | 8.96 | 4.48 | sorghum | 73 |
| | 8.96 | 0.56 | rice | * |
| | 8.96 | 1.12 | rice | * |
| | 8.96 | 2.24 | rice | 28 |
| | 8.96 | 4.48 | rice | 38 |
| Benzyl 2-chloro-4-trifluoro-methyl-5-thiazolecarboxylate | 8.96 | 0.56 | sorghum | 90 |
| | 8.96 | 1.12 | sorghum | 100 |
| | 8.96 | 2.24 | sorghum | 80 |
| | 8.96 | 4.48 | sorghum | 75 |
| | 8.96 | 0.56 | rice | 44 |
| | 8.96 | 1.12 | rice | 26 |
| | 8.96 | 2.24 | rice | * |
| | 8.96 | 4.48 | rice | * |
| Butoxyethyl 2-chloro-4-trifluoro-methyl-5-thiazolecarboxylate | 8.96 | 0.56 | sorghum | 80 |
| | 8.96 | 1.12 | sorghum | 85 |
| | 8.96 | 2.24 | sorghum | 80 |
| | 8.96 | 4.48 | sorghum | 70 |
| | 8.96 | 0.56 | rice | 39 |
| | 8.96 | 1.12 | rice | 26 |
| | 8.96 | 2.24 | rice | * |
| | 8.96 | 4.48 | rice | 23 |
| $\beta$-chloroethyl 2-chloro-4-trifluoro-methyl-5-thiazolecarboxylate | 8.96 | 0.56 | sorghum | 80 |
| | 8.96 | 1.12 | sorghum | 70 |
| | 8.96 | 2.24 | sorghum | 70 |
| | 8.96 | 4.48 | sorghum | 70 |
| | 8.96 | 0.56 | rice | 34 |
| | 8.96 | 1.12 | rice | 26 |
| | 8.96 | 2.24 | rice | * |
| | 8.96 | 4.48 | rice | * |
| 2-Chloro-4-trifluoromethyl-5-thiazolecarboxylic acid | 8.96 | 0.56 | sorghum | 68 |
| | 8.96 | 1.12 | sorghum | 73 |
| | 8.96 | 2.24 | sorghum | 51 |
| | 8.96 | 4.48 | sorghum | 43 |
| | 8.96 | 0.56 | rice | 55 |
| | 8.96 | 1.12 | rice | 35 |
| | 8.96 | 2.24 | rice | * |
| | 8.96 | 4.48 | rice | * |
| Ethyl 2-chloro-4-pentafluoro-ethyl-5-thiazolecarboxylate | 8.96 | 0.56 | sorghum | 25 |
| | 8.96 | 1.12 | sorghum | 65 |
| | 8.96 | 2.24 | sorghum | 50 |
| | 8.96 | 4.48 | sorghum | 48 |
| | 8.96 | 0.56 | rice | * |
| | 8.96 | 1.12 | rice | 25 |
| | 8.96 | 2.24 | rice | 35 |
| | 8.96 | 4.48 | rice | 30 |

*Safening effect was between 0 and 20

Table II summarizes the results obtained when the compounds of the invention were tested in accordance with the procedure of Example I utilizing butachlor as the herbicide.

Table II

| Safening Agent | Rate of Safening Agent (kg/h) | Rate of Herbicide | Crop | Safening Effect |
|---|---|---|---|---|
| Ethyl 2-chloro-4-isopropyl-5-thiazolecarboxylate | 8.96 | 4.48 | sorghum | 60 |
| | 8.96 | 4.48 | rice | 33 |
| Ethyl 2-chloro-4-ethyl-5-thiazolecarboxylate | 8.96 | 4.48 | sorghum | 60 |
| | 8.96 | 4.48 | rice | 70 |
| Ethyl 2-chloro-4-trifluoro-methyl-5-thiazolecarboxylate | 8.96 | 4.48 | sorghum | 75 |
| | 8.96 | 4.48 | rice | 20 |
| Ethyl 2-chloro-4-t-butyl-5-thiazolecarboxylate | 8.96 | 4.48 | sorghum | 28 |
| | 8.96 | 4.48 | rice | 70 |
| Butyl 2-chloro-4-trifluoro-methyl-5-thiazolecarboxylate | 8.96 | 4.48 | sorghum | 40 |
| | 8.96 | 4.48 | rice | 62 |
| Hexyl 2-chloro-4-trifluoro- | 8.96 | 4.48 | sorghum | 40 |

Table II-continued

| Safening Agent | Rate of Safening Agent (kg/h) | Rate of Herbicide | Crop | Safening Effect |
|---|---|---|---|---|
| methyl-5-thiazolecarboxylate | 8.96 | 4.48 | rice | 47 |
| Octyl 2-chloro-4-trifluoro- | 8.96 | 4.48 | sorghum | 40 |
| methyl-5-thiazolecarboxylate | 8.96 | 4.48 | rice | 37 |
| Phenyl 2-chloro-4-trifluoro- | 8.96 | 4.48 | sorghum | * |
| methyl-5-thiazolecarboxylate | 8.96 | 4.48 | rice | 55 |
| p-Chlorophenyl 2-chloro-4-tri- | 8.96 | 4.48 | sorghum | 20 |
| fluoromethyl-5-thiazolecarboxylate | 8.96 | 4.48 | rice | 55 |
| Ethyl 2-phenoxy-4-trifluoro- | 8.96 | 4.48 | sorghum | 28 |
| methyl-5-thiazolecarboxylate | 8.96 | 4.48 | rice | 68 |
| Ethyl 2-ethoxy-4-triethoxy- | 8.96 | 4.48 | sorghum | 28 |
| methyl-5-thiazolecarboxylate | 8.96 | 4.48 | rice | 50 |
| Allyl 2-chloro-4-trifluoro- | 8.96 | 4.48 | sorghum | * |
| methyl-5-thiazolecarboxylate | 8.96 | 4.48 | rice | 50 |
| 2-Chloro-4-trifluoromethyl- | 8.96 | 4.48 | sorghum | 62 |
| 5-thiazolecarboxylic acid | 8.96 | 4.48 | rice | 68 |
| Methyl 2-chloro-4-trifluoro- | 8.96 | 4.48 | sorghum | 62 |
| methyl-5-thiazolecarboxylate | 8.96 | 4.48 | rice | 53 |
| Isoropyl 2-chloro-4-trifluoro- | 8.96 | 4.48 | sorghum | 37 |
| methyl-5-thiazolecarboxylate | 8.96 | 4.48 | rice | * |
| Benzyl 2-chloro-4-trifluoromethyl- | 8.96 | 4.48 | sorghum | 22 |
| 5-thiazolecarboxylate | 8.96 | 4.48 | rice | 57 |
| Butoxyethyl 2-chloro-4-trifluoro- | 8.96 | 4.48 | sorghum | 67 |
| methyl-5-thiazolecarboxylate | 8.96 | 4.48 | rice | 57 |
| β-trichloroethyl 2-chloro-4-tri- | 8.96 | 4.48 | sorghum | 32 |
| fluoromethyl-5-thiazolecarboxylate | 8.96 | 4.48 | rice | 27 |
| Methyl 2-chloro-4-heptafluoro- | 8.96 | 4.48 | sorghum | * |
| propyl-5-thiazolecarboxylate | 8.96 | 4.48 | rice | 59 |
| Ethyl 2-chloro-4-pentafluoro- | 8.96 | 4.48 | sorghum | * |
| ethyl-5-thiazolecarboxylate | 8.96 | 4.48 | rice | 45 |
| Ethyl 2-bromo-4-trifluoro- | 8.96 | 4.48 | sorghum | * |
| methyl-5-thiazolecarboxylate | 8.96 | 4.48 | rice | 70 |
| Ethyl 2-iodo-4-trifluoromethyl- | 8.96 | 6.72 | sorghum | 23 |
| 5-thiazolecarboxylate | 8.96 | 6.72 | rice | 47 |
| 2-Chloro-4-trifluoromethyl-5- | 8.96 | 6.72 | sorghum | * |
| thiazolecarboxylic acid chloride | 8.96 | 6.72 | rice | * |
| N,N-diethyl-2-chloro-4-trifluoro- | 8.96 | 6.72 | sorghum | 45 |
| methyl-5-thiazolecarboxamide | 8.96 | 6.72 | rice | 70 |
| Ethyl 2-chloro-4-trichloromethyl- | 8.96 | 6.72 | sorghum | 33 |
| 5-thiazolecarboxylate | 8.96 | 6.72 | rice | 30 |
| Triethanolamine salt of 2-chloro-4- | 8.96 | 6.72 | sorghum | 20 |
| trifluoromethyl-5-thiazolecarboxylic acid | 8.96 | 6.72 | rice | * |
| Diethylamine salt of 2-chloro- | 8.96 | 6.72 | sorghum | 40 |
| 4-trifluoromethyl-5-thiazole- carboxylic acid | 8.96 | 6.72 | rice | * |
| Isoropylamine salt of 2-chloro- | 8.96 | 6.72 | sorghum | 35 |
| 4-trifluoromethyl-5-thiazole- carboxylic acid | 8.96 | 6.72 | rice | 20 |
| Ethyl 2-fluoro-4-trifluoromethyl- | 8.96 | 6.72 | sorghum | * |
| 5-thiazolecarboxylate | 8.96 | 6.72 | rice | 30 |

*Safening effect was between 0 and 20

EXAMPLE 2

A good grade of top soil is placed in a plastic pot. A measured quantity of the safening agent dispersed or dissolved in a suitable carrier is sprayed on the soil surface. A measured quantity of butachlor herbicide dissolved in a solvent is sprayed on the soil surface. Pre-soaked rice is seeded into the pots that were previously flooded with water. The pots are flooded at least up to the soil surface for the duration of the test. The plants are observed at the end of approximately 21 days and the results in terms of the percent inhibition of rice are recorded. As in Example 1, for each test pots are prepared containing soil treated only with butachlor. For each test, pots are also prepared containing soil treated only with the safening agent. The safening effect is determined in accordance with Example 1.

Table II summarizes the results obtained when the compounds of the invention were tested in accordance with the procedure of Example 2.

Table III

| Safening Agent | Rate of Safening Agent (kg/h) | Rate of Herbicide (kg/h) | Safening Effect |
|---|---|---|---|
| Ethyl 2-chloro-4-t-butyl-5- thiazolecarboxylate | 1.12 | 0.14 | 34 |
|  | 1.12 | 0.56 | * |
| Butyl 2-chloro-4-trifluoro- methyl-5-thiazolecarboxylate | 0.56 | 0.07 | * |
|  | 0.56 | 0.28 | 25 |
|  | 0.56 | 1.12 | * |
| Hexyl 2-chloro-4-trifluoro- methyl-5-thiazolecarboxylate | 0.56 | 0.07 | * |
|  | 0.56 | 0.28 | 25 |
| Octyl 2-chloro-4-trifluoro- | 0.56 | 0.07 | 24 |

Table III-continued

| Safening Agent | Rate of Safening Agent (kg/h) | Rate of Herbicide (kg/h) | Safening Effect |
|---|---|---|---|
| methyl-5-thiazolecarboxylate | 0.56 | 0.28 | 53 |
|  | 0.56 | 1.12 | 30 |
| Phenyl 2-chloro-4-trifluoro- | 0.56 | 0.07 | 30 |
| methyl-5-thiazolecarboxylate | 0.56 | 0.28 | 61 |
|  | 0.56 | 1.12 | 30 |
| p-Chlorophenyl 2-chloro-4-tri- | 0.56 | 0.07 | 29 |
| fluoromethyl-5-thiazolecarboxylate | 0.56 | 0.28 | 42 |
|  | 0.56 | 1.12 | 25 |
| Ethyl 2-phenoxy-4-trifluoro- | 0.56 | 0.07 | * |
| methyl-5-thiazolecarboxylate | 0.56 | 0.28 | 35 |
|  | 0.56 | 1.12 | * |
| Ethyl 2-ethoxy-4-triethoxy- | 0.56 | 0.07 | * |
| methyl-5-thiazolecarboxylate | 0.56 | 0.28 | * |
|  | 0.56 | 1.12 | * |
| Allyl 2-chloro-4-trifluoro- | 0.56 | 0.07 | * |
| methyl-5-thiazolecarboxylate | 0.56 | 0.28 | 40 |
|  | 0.56 | 1.12 | * |
| Ethyl 2-chloro-4-ethyl-5- | 1.12 | 0.14 | * |
| thiazolecarboxylate | 1.12 | 0.56 | * |
| 2-Chloro-4-trifluoromethyl- | 0.56 | 0.07 | 36 |
| 5-thiazolecarboxylic acid | 0.56 | 0.28 | 35 |
|  | 0.56 | 1.12 | * |
| Methyl 2-chloro-4-trifluoro- | 0.56 | 0.07 | 44 |
| methyl-5-thiazolecarboxylate | 0.56 | 0.28 | 67 |
|  | 0.56 | 1.12 | * |
| Benzyl 2-chloro-4-trifluoro- | 0.56 | 0.07 | 44 |
| methyl-5-thiazolecarboxylate | 0.56 | 0.28 | 75 |
|  | 0.56 | 1.12 | 20 |
| Butoxyethyl 2-chloro-4-trifluoro- | 0.56 | 0.07 | 46 |
| methyl-5-thiazolecarboxylate | 0.56 | 0.28 | 72 |
|  | 0.56 | 1.12 | * |
| β-chloroethyl 2-chloro-4-trifluoro- | 0.56 | 0.07 | 56 |
| methyl-5-thiazolecarboxylate | 0.56 | 0.28 | 75 |
|  | 0.56 | 1.12 | 30 |
| Ethyl 2-bromo-4-trifluoromethyl- | 0.56 | 0.07 | * |
| 5-thiazolecarboxylate | 0.56 | 0.28 | 70 |
|  | 0.56 | 1.12 | 32 |
| Ethyl 2-iodo-4-trifluoro- | 0.56 | 0.07 | * |
| methyl-5-thiazolecarboxylate | 0.56 | 0.28 | 50 |
|  | 0.56 | 1.12 | * |
| Ethyl 2-ethoxy-4-trifluoro- | 0.56 | 0.07 | * |
| methyl-5-thiazolecarboxylate | 0.56 | 0.28 | * |
|  | 0.56 | 1.12 | * |
| Ethyl 2-chloro-4-pentafluro- | 0.56 | 0.07 | 40 |
| ethyl-5-thiazolecarboxylate | 0.56 | 0.28 | 24 |
|  | 0.56 | 1.12 | * |
| N,N-diethyl-2-chloro-4-trifluoro- | 0.56 | 0.07 | 35 |
| methyl-5-thiazolecarboxamide | 0.56 | 0.28 | 59 |
|  | 0.56 | 1.12 | * |

*Safening effect was between 0 and 20

As noted previously, the 2,4-disubstituted-5-thiazolecarboxylates may be used to protect crops from the herbicidal activity of acetamide herbicides without a corresponding diminution in herbicidal activity to the weeds. Examples 3–6 are illustrative of such activity.

EXAMPLE 3

A good grade of top soil is placed in a plastic pot and compacted to a depth of approximately 1.27 cm. from the top of said pot. A predetermined number of crop seeds and weed seeds are placed on top of the soil. A cover layer, approximately 1.27 cm., is placed on top of said seeds. The soil is then treated with a mixture of the safening agent and alachlor dispersed or dissolved in a suitable solvent. For each test series, pots are treated with only the herbicide. Additionally, pots are treated with only the safening agent. The herbicidal effect is observed approximately 21 days after treatment.

Tables IV–IX summarize the results obtained when the compounds of the invention were tested in accordance with the procedure of Example 3. Each table represents the results of different tests using said procedure. Note that in each test a control is used in which the plants are treated with various rates of the herbicide alone.

Table IV

| Rate of Herbicide (kg/h) | Safening Agent | Rate of Safening Agent (kg/h) | Percent Inhibition | | | |
|---|---|---|---|---|---|---|
|  |  |  | Sorghum | Green Foxtail | Crab-grass | Barnyard Grass |
| 0.035 | — | — | 0 | 98 | 93 | 99 |
| 0.14 |  |  | 33 | 100 | 99 | 100 |
| 0.56 |  |  | 50 | 100 | 99 | 100 |
| 2.24 |  |  | 95 | 100 | 100 | 100 |
| — | Ethyl 2-chloro-4-isopropyl- | 0.14 | 0 | 0 | 0 | 0 |
| 0.035 | 5-thiazolecarboxylate | 0.14 | 0 | 95 | 97 | 93 |

Table IV-continued

| Rate of Herbicide (kg/h) | Safening Agent | Rate of Safening Agent (kg/h) | Percent Inhibition ||||
|---|---|---|---|---|---|---|
| | | | Sorghum | Green Foxtail | Crab-grass | Barnyard Grass |
| 0.14 | | 0.14 | 10 | 100 | 99 | 99 |
| 0.56 | | 0.14 | 8 | 99 | 99 | 99 |
| 2.24 | | 0.14 | 93 | 100 | 100 | 100 |
| — | Ethyl 2-chloro-4-isopropyl-5-thiazolecarboxylate | 0.56 | 0 | 0 | 0 | 0 |
| 0.035 | | 0.56 | 0 | 99 | 99 | 97 |
| 0.14 | | 0.56 | 3 | 99 | 99 | 100 |
| 0.56 | | 0.56 | 20 | 100 | 99 | 99 |
| 2.24 | | 0.56 | 68 | 100 | 100 | 100 |
| — | Ethyl 2-chloro-4-isopropyl-5-thiazolecarboxylate | 2.24 | 0 | 0 | 0 | 0 |
| 0.035 | | 2.24 | 0 | 99 | 93 | 97 |
| 0.14 | | 2.24 | 3 | 98 | 99 | 100 |
| 0.56 | | 2.24 | 25 | 100 | 99 | 100 |
| 2.24 | | 2.24 | 78 | 100 | 100 | 100 |

Table V

| Rate of Herbicide (kg/h) | Safening Agent | Rate of Safening Agent (kg/h) | Percent Inhibition ||||
|---|---|---|---|---|---|---|
| | | | Sorghum | Green Foxtail | Crab-grass | Barnyard Grass |
| 0.035 | — | — | 10 | 83 | 92 | 91 |
| 0.14 | | | 10 | 93 | 96 | 99 |
| 0.56 | | | 35 | 99 | 99 | 100 |
| 2.24 | | | 87 | 100 | 99 | 100 |
| — | Ethyl 2-chloro-4-t-butyl-5-thiazolecarboxylate | 0.14 | 3 | 0 | 3 | 0 |
| 0.035 | | 0.14 | 3 | 75 | 93 | 93 |
| 0.14 | | 0.14 | 10 | 90 | 96 | 99 |
| 0.56 | | 0.14 | 18 | 98 | 99 | 99 |
| 2.24 | | 0.14 | 65 | 100 | 99 | 100 |
| — | Ethyl 2-chloro-4-t-butyl-5-thiazolecarboxylate | 0.56 | 3 | 0 | 0 | 0 |
| 0.035 | | 0.56 | 3 | 53 | 90 | 89 |
| 0.14 | | 0.56 | 8 | 88 | 95 | 100 |
| 0.56 | | 0.56 | 30 | 97 | 98 | 100 |
| 2.24 | | 0.56 | 48 | 100 | 99 | 100 |

Table VI

| Rate of Herbicide (kg/h) | Safening Agent | Rate of Safening Agent (kg/h) | Percent Inhibition ||||
|---|---|---|---|---|---|---|
| | | | Sorghum | Green Foxtail | Crab-grass | Barnyard Grass |
| 0.035 | — | — | 0 | 17 | 83 | 96 |
| 0.14 | | | 32 | 70 | 97 | 98 |
| 0.56 | | | 77 | 97 | 99 | 99 |
| 2.24 | | | 92 | 98 | 99 | 100 |
| — | Ethyl 2-chloro-4-trifluoromethyl-5-thiazolecarboxylate | 0.14 | 0 | 0 | 0 | 0 |
| 0.035 | | 0.14 | 0 | 25 | 83 | 75 |
| 0.14 | | 0.14 | 10 | 68 | 99 | 99 |
| 0.56 | | 0.14 | 3 | 90 | 99 | 100 |
| 2.24 | | 0.14 | 40 | 100 | 99 | 100 |
| — | Ethyl 2-chloro-4-trifluoromethyl-5-thiazolecarboxylate | 0.56 | 0 | 0 | 0 | 0 |
| 0.035 | | 0.56 | 0 | 8 | 70 | 78 |
| 0.14 | | 0.56 | 0 | 73 | 99 | 97 |
| 0.56 | | 0.56 | 5 | 93 | 99 | 99 |
| 2.24 | | 0.56 | 15 | 100 | 100 | 100 |
| — | Ethyl 2-chloro-4-trifluoromethyl-5-thiazolecarboxylate | 2.24 | 0 | 0 | 0 | 0 |
| 0.035 | | 2.24 | 0 | 3 | 40 | 40 |
| 0.14 | | 2.24 | 0 | 58 | 90 | 99 |
| 0.56 | | 2.24 | 5 | 92 | 100 | 100 |
| 2.24 | | 2.24 | 5 | 99 | 100 | 100 |

Table VII

| Rate of Herbicide (kg/h) | Safening Agent | Rate of Safening Agent (kg/h) | Percent Inhibition ||||
|---|---|---|---|---|---|---|
| | | | Sorghum | Green Foxtail | Crab-grass | Barnyard Grass |
| 0.14 | — | — | 63 | 95 | 93 | 99 |
| 0.56 | | | 95 | 99 | 99 | 100 |
| 2.24 | | | 99 | 100 | 99 | 100 |
| — | Methyl 2-chloro-4-trifluoromethyl-5-thiazolecarboxylate | 0.14 | 10 | 0 | 0 | 0 |
| 0.14 | | 0.14 | 40 | 98 | 95 | 99 |
| 0.56 | | 0.14 | 55 | 99 | 99 | 100 |
| 2.24 | | 0.14 | 93 | 99 | 99 | 100 |
| — | Methyl 2-chloro-4-trifluoromethyl-5-thiazolecarboxylate | 0.56 | 0 | 0 | 0 | 0 |
| 0.14 | | 0.56 | 13 | 97 | 98 | 98 |

Table VII-continued

| Rate of Herbicide (kg/h) | Safening Agent | Rate of Safening Agent (kg/h) | Sorghum | Green Foxtail | Crab-grass | Barnyard Grass |
|---|---|---|---|---|---|---|
| 0.56 | | 0.56 | 55 | 99 | 99 | 100 |
| 2.24 | | 0.56 | 73 | 99 | 99 | 100 |
| — | Benzyl 2-chloro-4-trifluoro- | 0.14 | 0 | 0 | 0 | 0 |
| 0.14 | methyl-5-thiazolecarboxylate | 0.14 | 55 | 97 | 93 | 98 |
| 0.56 | | 0.14 | 65 | 99 | 99 | 100 |
| 2.24 | | 0.14 | 88 | 100 | 99 | 100 |
| — | Benzyl 2-chloro-4-trifluoro- | 0.56 | 0 | 0 | 0 | 0 |
| 0.14 | methyl-5-thiazolecarboxylate | 0.56 | 35 | 95 | 95 | 99 |
| 0.56 | | 0.56 | 58 | 99 | 99 | 100 |
| 2.24 | | 0.56 | 88 | 99 | 99 | 100 |
| — | Butoxyethyl 2-chloro-4-tri- | 0.14 | 0 | 0 | 0 | 0 |
| 0.14 | fluoromethyl-5-thiazole- | 0.14 | 28 | 97 | 97 | 100 |
| 0.56 | carboxylate | 0.14 | 70 | 99 | 99 | 100 |
| 2.24 | | 0.14 | 90 | 100 | 99 | 100 |
| — | Butoxyethyl 2-chloro-4-tri- | 0.56 | 0 | 0 | 0 | 0 |
| 0.14 | fluoromethyl-5-thiazole- | 0.56 | 40 | 97 | 95 | 99 |
| 0.56 | carboxylate | 0.56 | 58 | 98 | 98 | 99 |
| 2.24 | | 0.56 | 95 | 99 | 99 | 100 |
| — | 2'-Chloroethyl 2-chloro-4- | 0.14 | 0 | 0 | 0 | 0 |
| 0.14 | trifluoromethyl-5-thiazole- | 0.14 | 50 | 98 | 98 | 99 |
| 0.56 | carboxylate | 0.14 | 75 | 99 | 99 | 100 |
| 2.24 | | 0.14 | 88 | 99 | 99 | 100 |
| — | 2'-Chloroethyl 2-chloro-4- | 0.56 | 0 | 0 | 0 | 0 |
| 0.14 | trifluoromethyl-5-thiazole- | 0.56 | 13 | 98 | 98 | 99 |
| 0.56 | carboxylate | 0.56 | 58 | 98 | 99 | 99 |
| 2.24 | | 0.56 | 75 | 100 | 100 | 100 |

Table VIII

| Rate of Herbicide (kg/h) | Safening Agent | Rate of Safening Agent (kg/h) | Sorghum | Green Foxtail | Crab-grass | Barnyard Grass |
|---|---|---|---|---|---|---|
| 1.12 | — | — | 70 | 100 | 99 | 99 |
| 2.24 | | | 83 | 100 | 100 | 99 |
| 4.48 | | | 97 | 100 | 100 | 100 |
| — | Ethyl 2-phenoxy-4-trifluoro- | 8.96 | 0 | 0 | 0 | 0 |
| 1.12 | methyl-5-thiazolecarboxylate | 8.96 | 5 | 100 | 99 | 100 |
| 2.24 | | 8.96 | 8 | 100 | 100 | 100 |
| 4.48 | | 8.96 | 35 | 100 | 100 | 100 |
| — | 2-Chloro-4-trifluoromethyl- | 8.96 | 10 | 0 | 0 | 0 |
| 1.12 | 5-thiazolecarboxylic acid | 8.96 | 40 | 100 | 100 | 100 |
| 2.24 | | 8.96 | 60 | 100 | 100 | 100 |
| 4.48 | | 8.96 | 65 | 100 | 100 | 100 |
| — | Ethyl 2-chloro-4-pentafluoro- | 8.96 | 0 | 0 | 0 | 0 |
| 1.12 | ethyl-5-thiazolecarboxylate | 8.96 | 10 | 100 | 99 | 99 |
| 2.24 | | 8.96 | 50 | 100 | 100 | 100 |
| 4.48 | | 8.96 | 65 | 100 | 100 | 100 |
| — | Ethyl 2-bromo-4-trifluoro- | 8.96 | 0 | 0 | 0 | 0 |
| 1.12 | methyl-5-thiazolecarboxylate | 8.96 | 5 | 100 | 100 | 100 |
| 2.24 | | 8.96 | 13 | 100 | 100 | 100 |
| 4.48 | | 8.96 | 38 | 100 | 100 | 100 |
| — | Ethyl 2-ethoxy-4-trifluoro- | 8.96 | 0 | 0 | 0 | 0 |
| 1.12 | methyl-5-thiazolecarboxylate | 8.96 | 15 | 100 | 100 | 99 |
| 2.24 | | 8.96 | 33 | 100 | 100 | 100 |
| 4.48 | | 8.96 | 40 | 100 | 100 | 100 |
| — | Ethyl 2-chloro-4-trichloro- | 8.96 | 0 | 0 | 0 | 0 |
| 1.12 | methyl-5-thiazolecarboxylate | 8.96 | 25 | 100 | 99 | 99 |
| 2.24 | | 8.96 | 60 | 100 | 100 | 100 |
| 4.48 | | 8.96 | 80 | 100 | 100 | 100 |
| — | N,N-diethyl-2-chloro-4-tri- | 8.96 | 0 | 0 | 0 | 0 |
| 1.12 | fluoromethyl-5-thiazole- | 8.96 | 80 | 100 | 100 | 100 |
| 2.24 | carboxamide | 8.96 | 98 | 100 | 100 | 100 |
| 4.48 | | 8.96 | 98 | 100 | 100 | 100 |
| — | Triethanolamine salt of 2- | 8.96 | 5 | 100 | 99 | 99 |
| 1.12 | chloro-4-trifluoromethyl-5- | 8.96 | 68 | 100 | 100 | 100 |
| 2.24 | thiazolecarboxylic acid | 8.96 | 94 | 100 | 100 | 100 |
| 4.48 | | 8.96 | 100 | 100 | 100 | 100 |

Table IX

| Rate of Herbicide (kg/h) | Safening Agent | Rate of Safening Agent (kg/h) | Rice | Sorghum | Barnyard Grass | Crab-grass | Panicum | Green Foxtail |
|---|---|---|---|---|---|---|---|---|
| 1.12 | — | — | 78 | 58 | 100 | 99 | 100 | 99 |

Table IX-continued

| Rate of Herbicide (kg/h) | Safening Agent | Rate of Safening Agent (kg/h) | Rice | Sorghum | Barnyard Grass | Crabgrass | Panicum | Green Foxtail |
|---|---|---|---|---|---|---|---|---|
| 2.24 | | | 85 | 99 | 100 | 100 | 100 | 100 |
| 4.48 | | | 97 | 99 | 100 | 100 | 100 | 100 |
| — | Ethyl 2-chloro-4- | 8.96 | 0 | 0 | 0 | 0 | 0 | 0 |
| 1.12 | methyl-5-thiazole- | 8.96 | 78 | 30 | 100 | 100 | 100 | 100 |
| 2.24 | carboxylate | 8.96 | 73 | 28 | 100 | 100 | 100 | 100 |
| 4.48 | | 8.96 | 90 | 55 | 100 | 100 | 100 | 100 |
| — | Ethyl 2-chloro-4- | 8.96 | 0 | 0 | 0 | 0 | 0 | 0 |
| 1.12 | trifluoromethyl-5- | 8.96 | 73 | 3 | 100 | 100 | 99 | 99 |
| 2.24 | thiazolecarboxylate | 8.96 | 78 | 23 | 100 | 100 | 100 | 100 |
| 4.48 | | 8.96 | 85 | 30 | 100 | 100 | 100 | 100 |
| — | Ethyl 2-chloro-4- | 8.96 | 0 | 0 | 0 | 0 | 0 | 0 |
| 1.12 | ethyl-5-thiazole- | 8.96 | 60 | 30 | 100 | 99 | 100 | 99 |
| 2.24 | carboxylate | 8.96 | 85 | 75 | 100 | 100 | 100 | 100 |
| 4.48 | | 8.96 | 88 | 73 | 100 | 100 | 100 | 100 |

EXAMPLE 4

The procedure of Example 3 is repeated wherein the herbicide used is butachlor. Table X summarizes results obtained in accordance with this procedure.

Table X

| Rate of Herbicide (kg/h) | Safening Agent | Rate of Safening Agent (kg/h) | Rice | Sorghum | Barnyard Grass | Crabgrass | Panicum | Green Foxtail |
|---|---|---|---|---|---|---|---|---|
| 2.24 | — | — | 50 | 50 | 100 | 100 | 99 | 100 |
| 4.48 | | | 78 | 60 | 100 | 100 | 100 | 100 |
| 8.96 | | | 93 | 88 | 100 | 100 | 100 | 100 |
| 2.24 | Ethyl 2-chloro-4- | 8.96 | 33 | 8 | 100 | 100 | 100 | 100 |
| 4.48 | methyl-5-thiazole- | 8.96 | 53 | 18 | 100 | 100 | 100 | 100 |
| 8.96 | carboxylate | 8.96 | 80 | 28 | 100 | 100 | 100 | 100 |
| 2.24 | Ethyl 2-chloro-4- | 8.96 | 20 | 0 | 100 | 100 | 100 | 100 |
| 4.48 | trifluoromethyl-5- | 8.96 | 55 | 20 | 100 | 100 | 100 | 100 |
| 8.96 | thiazolecarboxylate | 8.96 | 68 | 13 | 100 | 100 | 100 | 100 |
| 2.24 | Ethyl 2-chloro-4- | 8.96 | 20 | 13 | 100 | 100 | 100 | 100 |
| 4.48 | ethyl-5-thiazole- | 8.96 | 20 | 15 | 100 | 100 | 100 | 100 |
| 8.96 | carboxylate | 8.96 | 53 | 20 | 100 | 100 | 100 | 100 |

EXAMPLE 5

5.08 cm. of a good grade of top soil is placed in a 7.62 cm. deep plastic pot. A predetermined number of barnyard grass seeds are applied to the soil surface. A measured quantity of the safening agent dispersed or dissolved in a suitable carrier is sprayed on the soil surface. A measured quantity of butachlor herbicide dissolved in a solvent is sprayed on the soil surface. Pre-soaked rice is seeded into the pots that were previously flooded with water. The pots are flooded just above the soil surface for the duration of the test. The plants are observed at the end of approximately 21 days and the results in terms of percent inhibition recorded. For each test, a pot is prepared containing soil treated only with butachlor. For each test, pots are prepared containing soil treated only with the safening agent. Tables XI, XII and XIII represent the results of three separate tests conducted in accordance with the procedure of Example 5.

Table XI

| Rate of Herbicide (kg/h) | Safening Agent | Rate of Safening Agent (kg/h) | Rice | Barnyard Grass |
|---|---|---|---|---|
| 0.07 | — | — | 31 | 99 |
| 0.28 | | | 74 | 100 |
| 1.12 | | | 98 | 100 |
| — | Phenyl 2-chloro-4-tri- | 0.07 | 0 | 0 |
| 0.07 | fluoromethyl-5-thiazole- | 0.07 | 0 | 97 |
| 0.28 | carboxylate | 0.07 | 38 | 99 |
| 1.12 | | 0.07 | 90 | 100 |
| — | Phenyl 2-chloro-4-tri- | 0.28 | 0 | 0 |
| 0.07 | fluoromethyl-5-thiazole- | 0.28 | 8 | 98 |
| 0.28 | carboxylate | 0.28 | 25 | 99 |
| 1.12 | | 0.28 | 68 | 100 |
| — | Phenyl 2-chloro-4-tri- | 1.12 | 0 | 0 |
| 0.07 | fluoromethyl-5-thiazole- | 1.12 | 0 | 92 |
| 0.28 | carboxylate | 1.12 | 23 | 100 |
| 1.12 | | 1.12 | 63 | 100 |
| — | Methyl 2chloro-4-tri- | 0.07 | 0 | 0 |
| 0.07 | fluoromethyl-5-thiazole- | 0.07 | 5 | 95 |
| 0.28 | carboxylate | 0.07 | 68 | 99 |
| 1.12 | | 0.07 | 95 | 100 |
| — | Methyl 2-chloro-4-tri- | 0.28 | 0 | 0 |
| 0.07 | fluoromethyl-5-thiazole- | 0.28 | 0 | 98 |
| 0.28 | carboxylate | 0.28 | 35 | 99 |
| 1.12 | | 0.28 | 68 | 100 |
| — | Methyl 2-chloro-4-tri- | 1.12 | 0 | 0 |
| 0.07 | fluoromethyl-5-thiazole- | 1.12 | 0 | 97 |
| 0.28 | carboxylate | 1.12 | 20 | 99 |
| 1.12 | | 1.12 | 55 | 100 |

Table XII

| Rate of Herbicide (Kg/h) | Safening Agent | Rate of Safening Agent (kg/h) | Percent Inhibition Rice | Percent Inhibition Barnyard Grass |
|---|---|---|---|---|
| 0.07 | — | — | 56 | 91 |
| 0.28 | | | 94 | 99 |
| 1.12 | | | 100 | 100 |
| — | Octyl 2-chloro-4-tri- | 0.07 | 0 | 0 |
| 0.07 | fluoromethyl-5-thiazole- | 0.07 | 40 | 85 |
| 0.28 | carboxylate | 0.07 | 73 | 99 |
| 1.12 | | 0.07 | 99 | 100 |
| — | Octyl 2-chloro-4-tri- | 0.28 | 0 | 0 |
| 0.07 | fluoromethyl-5-thiazole- | 0.28 | 5 | 90 |
| 0.28 | carboxylate | 0.28 | 73 | 99 |
| 1.12 | | 0.28 | 97 | 100 |
| — | Octyl 2-chloro-4-tri- | 1.12 | 0 | 0 |
| 0.07 | fluoromethyl-5-thiazole- | 1.12 | 15 | 97 |
| 0.28 | carboxylate | 1.12 | 70 | 99 |
| 1.12 | | 1.12 | 99 | 100 |
| — | Butoxyethyl 2-chloro-4- | 0.07 | 0 | 0 |
| 0.07 | trifluoromethyl-5-thia- | 0.07 | 43 | 92 |
| 0.28 | zolecarboxylate | 0.07 | 83 | 99 |
| 1.12 | | 0.07 | 100 | 100 |
| — | Butoxyethyl 2-chloro-4- | 0.28 | 0 | 0 |
| 0.07 | trifluoromethyl-5-thia- | 0.28 | 18 | 93 |
| 0.28 | zolecarboxylate | 0.28 | 48 | 99 |
| 1.12 | | 0.28 | 95 | 100 |
| — | Butoxyethyl 2-chloro-4- | 1.12 | 0 | 0 |
| 0.07 | trifluoromethyl-5-thia- | 1.12 | 0 | 90 |
| 0.28 | zolecarboxylate | 1.12 | 48 | 99 |
| 1.12 | | 1.12 | 97 | 100 |
| — | β-chloroethyl 2-chloro- | 0.07 | 0 | 0 |
| 0.07 | 4-trifluoromethyl-5- | 0.07 | 30 | 95 |
| 0.28 | thiazolecarboxylate | 0.07 | 53 | 99 |
| 1.12 | | 0.07 | 98 | 100 |
| — | β-chloroethyl 2-chloro- | 0.28 | 0 | 0 |
| 0.07 | 4-trifluoromethyl-5- | 0.28 | 5 | 93 |
| 0.28 | thiazolecarboxylate | 0.28 | 48 | 99 |
| 1.12 | | 0.28 | 98 | 100 |
| — | β-chloroethyl 2-chloro- | 1.12 | 0 | 0 |
| 0.07 | 4-trifluoromethyl-5- | 1.12 | 0 | 83 |
| 0.28 | thiazolecarboxylate | 1.12 | 20 | 99 |
| 1.12 | | 1.12 | 85 | 100 |

Table XIII

| Rate of Herbicide (kg/h) | Safening Agent | Rate of Safening Agent (kg/h) | Percent Inhibition* Rice | Percent Inhibition* Barnyard Grass |
|---|---|---|---|---|
| 0.07 | — | — | 65 | 95 |
| 0.28 | | | 93 | 100 |
| 1.12 | | | 100 | 100 |
| — | Methyl 2-chloro-4- | 0.56 | 0 | 0 |
| 0.07 | heptafluoropropyl-5- | 0.56 | 55 | 99 |
| 0.28 | thiazolecarboxylate | 0.56 | 100 | 100 |
| 1.12 | | 0.56 | 100 | 100 |

*Mean of two replicates

EXAMPLE 6

A good grade of top soil is placed in a container and compacted to a depth of approximately 1.27 cm. from the top of said container. A predetermined number of sorghum, green foxtail, crabgrass and barnyard grass were applied to the soil surface. The seeds were then covered with top soil and the surface was treated with a mixture of the herbicide and safening agent. The plants are observed at the end of approximately 18 days and the results in terms of percent inhibition recorded. Table XIV summarizes the results of tests conducted in accordance with Example 6.

Table XIV

| Herbicide | Rate of Herbicide (kg/h) | Safening Agent | Rate of Safening Agent (kg/h) | Sorghum | Green Foxtail | Crab-grass | Barnyard Grass |
|---|---|---|---|---|---|---|---|
| Alachlor | 0.14 | — | — | 10 | 99 | 95 | 100 |
| Alachlor | 0.56 | — | — | 80 | 99 | 99 | 100 |
| Alachlor | 2.24 | — | — | 85 | 100 | 100 | 100 |
| — | — | Ethyl 2-chloro-4-tri-fluoromethyl-5-thia-zolecarboxylate | 0.14 | 0 | 0 | 0 | 0 |
| — | — | Ethyl 2-chloro-4-tri-fluoromethyl-5-thia-zolecarboxylate | 0.56 | 5 | 0 | 0 | 0 |
| — | — | Ethyl 2-chloro-4-tri-fluoromethyl-5-thia-zolecarboxylate | 2.24 | 15 | 0 | 0 | 0 |
| Alachlor | 0.14 | Ethyl 2-chloro-4-tri-fluoromethyl-5-thia-zolecarboxylate | 0.14 | 0 | 99 | 99 | 99 |
| Alachlor | 0.56 | Ethyl 2-chloro-4-tri-fluoromethyl-5-thia-zolecarboxylate | 0.14 | 20 | 99 | 99 | 100 |
| Alachlor | 2.24 | Ethyl 2-chloro-4-tri-fluoromethyl-5-thia-zolecarboxylate | 0.14 | 55 | 100 | 100 | 100 |
| Alachlor | 0.14 | Ethyl 2-chloro-4-tri-fluoromethyl-5-thia-zolecarboxylate | 0.56 | 0 | 98 | 99 | 99 |
| Alachlor | 0.56 | Ethyl 2-chloro-4-tri-fluoromethyl-5-thia-zolecarboxylate | 0.56 | 5 | 99 | 99 | 99 |
| Alachlor | 2.24 | Ethyl 2-chloro-4-tri-fluoromethyl-5-thia-zolecarboxylate | 0.56 | 55 | 100 | 100 | 99 |
| Alachlor | 0.14 | Ethyl 2-chloro-4-tri-fluoromethyl-5-thia-zolecarboxylate | 2.24 | 25 | 97 | 98 | 99 |
| Alachlor | 0.56 | Ethyl 2-chloro-4-tri-fluoromethyl-5-thia-zolecarboxylate | 2.24 | 13 | 100 | 99 | 99 |
| Alachlor | 2.24 | Ethyl 2-chloro-4-tri-fluoromethyl-5-thia-zolecarboxylate | 2.24 | 38 | 100 | 100 | |
| 2-Chloro-N-(2-methoxy-1-methyl-ethyl)-6'-ethyl-o-acetotoluidide | 0.14 | — | — | 13 | 97 | 97 | 98 |
| 2-Chloro-N-(2-methoxy-1-methyl-ethyl)-6'-ethyl-o-acetotoluidide | 0.56 | — | — | 60 | 98 | 99 | 99 |
| 2-Chloro-N-(2-methoxy-1-methyl-ethyl)-6'-ethyl-o-acetotoluidide | 2.24 | — | — | 84 | 99 | 100 | 100 |

Table XIV-continued

| Herbicide | Rate of Herbicide (kg/h) | Safening Agent | Rate of Safening Agent (kg/h) | Percent Inhibition | | | |
|---|---|---|---|---|---|---|---|
| | | | | Sorghum | Green Foxtail | Crab-grass | Barnyard Grass |
| 2-Chloro-N-(2-methoxy-1-methyl-ethyl)-6'-ethyl-o-ace-totoluidide | 0.14 | Ethyl 2-chloro-4-tri-fluoromethyl-5-thia-zolecarboxylate | 0.14 | 0 | 98 | 98 | 98 |
| | 0.56 | | 0.14 | 0 | 99 | 99 | 99 |
| | 2.24 | Ethyl 2-chloro-4-tri-fluoromethyl-5-thia-zolecarboxylate | 0.14 | 70 | 100 | 100 | 100 |
| 2-Chloro-N-(2-methoxy-1-methyl-ethyl)-6'-ethyl-o-ace-totoluidide | 0.14 | Ethyl 2-chloro-4-tri-fluoromethyl-5-thia-zolecarboxylate | 0.56 | 8 | 98 | 97 | 98 |
| | 0.56 | | 0.56 | 10 | 99 | 99 | 99 |
| | 2.24 | Ethyl 2-chloro-4-tri-fluoromethyl-5-thia-zolecarboxylate | 0.56 | 15 | 100 | 100 | 100 |
| 2-Chloro-N-(2-methoxy-1-methyl-ethyl)-6'-ethyl-o-ace-totoluidide | 0.14 | Ethyl 2-chloro-4-tri fluoromethyl-5-thia-zolecarboxylate | 2.24 | 10 | 98 | 98 | 00 |
| | 0.56 | | 2.24 | 10 | 100 | 99 | 100 |
| | 2.24 | Ethyl 2-chloro-4-tri-fluoromethyl-5-thia-zolecarboxylate | 2.24 | 15 | 100 | 100 | 100 |

EXAMPLE 7

A predetermined number of corn, sorghum and rice seeds were placed on top of a good grade of top soil. The over layer was then treated with an appropriate amount of safening agent. A cover layer of soil treated with the appropriate herbicide was placed on top of the seeds. The plants were observed at the end of approximately 21 days and the results in terms of percent inhibition recorded. Table XV summarizes the results of tests conducted in accordance with Example 7.

Table XV

| Herbicide | Rate of Herbicide (kg/h) | Safening Agent | Rate of Safening Agent (kg/h) | Percent Inhibition | | |
|---|---|---|---|---|---|---|
| | | | | Sorghum | Rice | Corn |
| Alachlor | 0.56 | — | — | 88 | 98 | 0 |
| Alachlor | 4.48 | — | — | 99 | 100 | 25 |
| — | — | Ethyl 2-chloro-4-tri-fluoromethyl-5-thiazole-carboxylate | 8.96 | 0 | 0 | 0 |
| Alachlor | 0.56 | Ethyl 2-chloro-4-tri-fluoromethyl-5-thiazole-carboxylate | 8.96 | 5 | 83 | 0 |
| Alachlor | 4.48 | Ethyl 2-chloro-4-tri-fluoromethyl-5-thiazole-carboxylate | 8.96 | 58 | 100 | 30 |
| Butachlor | 1.12 | — | — | 30 | 20 | 0 |
| Butachlor | 8.96 | — | — | 85 | 95 | 20 |
| Butachlor | 1.12 | Ethyl 2-chloro-4-tri-fluoromethyl-5-thiazole-carboxylate | 8.96 | 0 | 0 | 0 |
| Butachlor | 8.96 | Ethyl 2-chloro- 4-tri-fluoromethyl-5-thiazole-carboxylate | 8.96 | 25 | 38 | 33 |
| 2-Chloro-N-(2-methoxy-1-methyl-ethyl)-6'-ethyl-o-ace-Totoluide | 0.56 | — | — | 50 | 73 | 8 |
| | 4.48 | — | — | 97 | 100 | 43 |
| | 0.56 | Ethyl 2-chloro-4-tri-fluoromethyl-5-thiazole-carboxylate | 8.96 | 0 | 55 | 10 |
| totoluide | 4.48 | | 8.96 | 75 | 100 | 10 |

As noted above, crop plants may be protected from herbicidal activity by treating the crop seed with the safening agent prior to planting. Example 8 illustrates such activity.

EXAMPLE 8

Sorghum seeds were treated with a solution of the appropriate safeing agent in dichloromethane. The solvent was evaporated which left only the safening agent on the seed. Untreated and treated sorghum seeds were planted in pots. Selected weed species were planted in separate pots. 1.27 cm. deep soil cover layer was placed on the pre-seeded pots. The soil surface was then treated with the herbicide. Approximately 21 days later, the results were observed and recorded. Table XVI summarizes the results observed when tests were conducted in accordance with Example 8.

Table XVI

| Herbicide | Rate of Herbicide (kg/h) | Safening Agent | Percent Sorghum Inhibition Seed Treatment Concentration (grams of safening agent/kilograms of seed) | | | |
|---|---|---|---|---|---|---|
| | | | 0 | 0.6 | 2.5 | 10 |
| Alachlor | — | Ethyl 2-chloro-4-trifluoromethyl-5-thiazolecarboxylate | 0 | 0 | 0 | 15 |
| Alachlor | 0.14 | Ethyl 2-chloro-4-trifluoromethyl-5-thiazolecarboxylate | 83 | 0 | 0 | 13 |
| Alachlor | 0.56 | Ethyl 2-chloro-4-trifluoromethyl-5-thiazolecarboxylate | 96 | 0 | 0 | 25 |
| Alachlor | 2.24 | Ethyl 2-chloro-4-trifluoromethyl-5-thiazolecarboxylate | 98 | 18 | 13 | 35 |
| Alachlor | — | Ethyl 2-chloro-4-t-butyl-5-thiazolecarboxylate | 0 | 0 | 5 | 25 |
| Alachlor | 0.14 | Ethyl 2-chloro-4-t-butyl-5-thiazolecarboxylate | 23 | 3 | 0 | 10 |
| Alachlor | 0.56 | Ethyl 2-chloro-4-t-butyl-5-thiazolecarboxylate | 65 | 0 | 0 | 0 |
| Alachlor | 2.24 | Ethyl 2-chloro-4-t-butyl-5-thiazolecarboxylate | 80 | 30 | 28 | 28 |
| 2-Chloro-N-(2-methoxy-1-methylethyl)-6'-ethyl-o-acetotoluidide | — | Ethyl 2-chloro-4-trifluoromethyl-5-thiazolecarboxylate | 0 | 0 | 0 | 20 |
| 2-Chloro-N-(2-methoxy-1-methylethyl)-6'-ethyl-o-acetotoluidide | 0.07 | Ethyl 2-chloro-4-trifluoromethyl-5-thiazolecarboxylate | 0 | 0 | 0 | 23 |
| 2-Chloro-N-(2-methoxy-1-methylethyl)-6'-ethyl-o-acetotoluidide | 0.14 | Ethyl 2-chloro-4-trifluoromethyl-5-thiazolecarboxylate | 5 | 0 | 0 | 15 |
| 2-Chloro-N-(2-methoxy-1-methylethyl)-6'-ethyl-o-acetotoluidide | 0.28 | Ethyl 2-chloro-4-trifluoromethyl-5-thiazolecarboxylate | 0 | 0 | 0 | 45 |
| 2-Chloro-N-(2-methoxy-1-methylethyl)-6'-ethyl-o-acetotoluidide | 0.56 | Ethyl 2-chloro-4-trifluoromethyl-5-thiazolecarboxylate | 25 | 0 | 0 | 25 |
| 2-Chloro-N-(2-methoxy-1-methylethyl)-6'-ethyl-o-acetotoluidide | 1.12 | Ethyl 2-chloro-4-trifluoromethyl-5-thiazolecarboxylate | 40 | 5 | 0 | 35 |
| 2-Chloro-N-(2-methoxy-1-methylethyl)-6'-ethyl-o-acetotoluidide | 2.24 | Ethyl-2-chloro-4-trifluoromethyl-5-thiazolecarboxylate | 73 | 15 | 13 | 23 |
| Alachlor | — | Butyl 2-chloro-4-trifluoromethyl-5-thiazolecarboxylate | 0 | 0 | 0 | 10 |
| Alachlor | 0.28 | Butyl 2-chloro-4-trifluoromethyl-5-thiazolecarboxylate | 83 | 0 | 5 | 13 |
| Alachlor | 1.12 | Butyl 2-chloro-4-trifluoromethyl-5-thiazolecarboxylate | 96 | 5 | 8 | 15 |
| Alachlor | 4.48 | Butyl 2-chloro-4-trifluoromethyl-5-thiazolecarboxylate | 98 | 13 | 8 | 18 |
| Alachlor | — | Hexyl 2-chloro-4-trifluoromethyl-5-thiazolecarboxylate | 0 | 0 | 5 | 18 |
| Alachlor | 0.28 | Hexyl 2-chloro-4-trifluoromethyl-5-thiazolecarboxylate | 83 | 8 | 13 | 30 |
| Alachlor | 1.12 | Hexyl 2-chloro-4-trifluoromethyl-5-thiazolecarboxylate | 96 | 8 | 13 | 33 |
| Alachlor | 4.48 | Hexyl 2-chloro-4-trifluoromethyl-5-thiazolecarboxylate | 98 | 13 | 15 | 35 |
| Alachlor | — | Octyl 2-chloro-4-trifluoromethyl-5-thiazolecarboxylate | 0 | 0 | 0 | 13 |
| Alachlor | 0.28 | Octyl 2-chloro-4-trifluoromethyl-5-thiazolecarboxylate | 83 | 10 | 10 | 13 |
| Alachlor | 1.12 | Octyl 2-chloro-4-trifluoromethyl-5-thiazolecarboxylate | 96 | 8 | 5 | 10 |
| Alachlor | 4.48 | Octyl 2-chloro-4-trifluoromethyl-5-thiazolecarboxylate | 98 | 25 | 23 | 23 |
| Alachlor | — | Phenyl 2-chloro-4-trifluoromethyl-5-thiazolecarboxylate | 0 | 0 | 0 | 10 |
| Alachlor | 0.28 | Phenyl 2-chloro-4-trifluoromethyl-5-thiazolecarboxylate | 83 | 10 | 10 | 18 |

Table XVI-continued

| Herbicide | Rate of Herbicide (kg/h) | Safening Agent | Percent Sorghum Inhibition Seed Treatment Concentration (grams of safening agent/kilograms of seed) | | | |
|---|---|---|---|---|---|---|
| | | | 0 | 0.6 | 2.5 | 10 |
| Alachlor | 1.12 | Phenyl 2-chloro-4-trifluoromethyl-5-thiazolecarboxylate | 96 | 5 | 5 | 20 |
| Alachlor | 4.48 | Phenyl 2-chloro-4-trifluoromethyl-5-thiazolecarboxylate | 98 | 13 | 15 | 35 |
| Alachlor | — | Ethyl 2-phenoxy-4-trifluoromethyl-5-thiazolecarboxylate | 0 | 0 | 0 | 5 |
| Alachlor | 0.28 | Ethyl 2-phenoxy-4-trifluoromethyl-5-thiazolecarboxylate | 83 | 0 | 0 | 5 |
| Alachlor | 1.12 | Ethyl 2-phenoxy-4-trifluoromethyl-5-thiazolecarboxylate | 96 | 33 | 30 | 23 |
| Alachlor | 4.48 | Ethyl 2-phenoxy-4-trifluoromethyl-5-thiazolecarboxylate | 98 | 88 | 88 | 90 |
| Alachlor | — | Allyl 2-chloro-4-trifluoromethyl-5-thiazolecarboxylate | 0 | 0 | 0 | — |
| Alachlor | 0.28 | Allyl 2-chloro-4-trifluoromethyl-5-thiazolecarboxylate | 83 | 0 | 5 | — |
| Alachlor | 1.12 | Allyl 2-chloro-4-trifluoromethyl-5-thiazolecarboxylate | 96 | 13 | 10 | — |
| Alachlor | 4.48 | Allyl 2-chloro-4-trifluoromethyl-5-thiazolecarboxylate | 98 | 23 | 20 | — |
| Alachlor | — | 2-Chloro-4-trifluoromethyl-5-thiazolecarboxylic acid | 0 | 0 | 10 | 20 |
| Alachlor | 0.28 | 2-Chloro-4-trifluoromethyl-5-thiazolecarboxylic acid | 83 | 10 | 13 | 35 |
| Alachlor | 1.12 | 2-Chloro-4-trifluoromethyl-5-thiazolecarboxylic acid | 96 | 10 | 10 | 38 |
| Alachlor | 4.48 | 2-Chloro-4-trifluoromethyl-5-thiazolecarboxylic acid | 98 | 18 | 18 | 40 |
| Alachlor | — | Isopropyl 2-chloro-4-trifluoromethyl-5-thiazolecarboxylate | 0 | 0 | 5 | 30 |
| Alachlor | 0.28 | Isopropyl 2-chloro-4-trifluoromethyl-5-thiazolecarboxylate | 83 | 0 | 0 | 20 |
| Alachlor | 1.12 | Isopropyl 2-chloro-4-trifluoromethyl-5-thiazolecarboxylate | 96 | 0 | 10 | 30 |
| Alachlor | 4.48 | Isopropyl 2-chloro-4-trifluoromethyl-5-thiazolecarboxylate | 98 | 23 | 28 | 58 |
| Alachlor | — | $\beta$-trichloroethyl 2-chloro-4-trifluoromethyl-5-thiazolecarboxylate | 0 | 0 | 5 | 13 |
| Alachlor | 0.28 | $\beta$-trichloroethyl 2-chloro-4-trifluoromethyl-5-thiazolecarboxylate | 93 | 10 | 13 | 30 |
| Alachlor | 1.12 | $\beta$-trichloroethyl 2-chloro-4-trifluoromethyl 5-thiazolecarboxylate | 93 | 5 | 13 | 23 |
| Alachlor | 4.48 | $\beta$-trichloroethyl 2-chloro-4-trifluoromethyl-5-thiazolecarboxylate | 96 | 20 | 20 | 23 |
| Alachlor | — | Methyl 2-chloro-4-trifluoromethyl-5-thiazolecarboxylate | 0 | 0 | 13 | 22 |
| Alachlor | 0.28 | Methyl 2-chloro-4-trifluoromethyl-5-thiazolecarboxylate | 85 | 0 | 15 | 23 |
| Alachlor | 1.12 | Methyl 2-chloro-4-trifluoromethyl-5-thiazolecarboxylate | 98 | 55 | 40 | 50 |
| Alachlor | 4.48 | Methyl 2-chloro-4-trifluoromethyl-5-thiazolecarboxylate | 98 | 83 | 65 | 63 |
| Alachlor | — | Benzyl 2-chloro-4-trifluoromethyl-5-thiazolecarboxylate | 0 | 0 | 13 | 20 |
| Alachlor | 0.28 | Benzyl 2-chloro-4-trifluoromethyl-5-thiazolecarboxylate | 85 | 0 | 15 | 23 |
| Alachlor | 1.12 | Benzyl 2-chloro-4-trifluoromethyl-5-thiazolecarboxylate | 98 | 30 | 35 | 45 |
| Alachlor | 4.48 | Benzyl 2-chloro-4-trifluoromethyl-5-thiazolecarboxylate | 98 | 80 | 65 | 63 |
| Alachlor | — | Butoxyethyl 2-chloro-4-trifluoromethyl-5-thiazolecarboxylate | 0 | 0 | 10 | 20 |
| Alachlor | 0.28 | Butoxyethyl 2-chloro-4-trifluoromethyl-5-thiazolecarboxylate | 85 | 0 | 10 | 23 |
| Alachlor | 1.12 | Butoxyethyl 2-chloro-4-trifluoromethyl-5-thiazolecarboxylate | 97 | 55 | 45 | 63 |
| Alachlor | 4.48 | Butoxyethyl 2-chloro-4-trifluoromethyl-5-thiazolecarboxylate | 98 | 78 | 63 | 63 |

Table XVI-continued

| Herbicide | Rate of Herbicide (kg/h) | Safening Agent | Percent Sorghum Inhibition Seed Treatment Concentration (grams of safening agent/kilograms of seed) | | | |
|---|---|---|---|---|---|---|
| | | | 0 | 0.6 | 2.5 | 10 |
| Alachlor | — | β-chloroethyl 2-chloro-4-trifluoromethyl-5-thiazolecarboxylate | 0 | 0 | 18 | 48 |
| Alachlor | 0.28 | β-chloroethyl 2-chloro-4-trifluoromethyl-5-thiazolecarboxylate | 85 | 10 | 23 | 50 |
| Alachlor | 1.12 | β-chloroethyl 2-chloro-4-trifluoromethyl-5-thiazolecarboxylate | 98 | 30 | 40 | 65 |
| Alachlor | 4.48 | β-chloroethyl 2-chloro-4-trifluoromethyl-5-thiazolecarboxylate | 98 | 75 | 65 | 70 |
| Alachlor | — | Ethyl 2-bromo-4-trifluoromethyl-5-thiazolecarboxylate | 0 | 0 | 15 | 30 |
| Alachlor | 0.28 | Ethyl 2-bromo-4-trifluoromethyl-5-thiazolecarboxylate | 85 | 18 | 28 | 55 |
| Alachlor | 1.12 | Ethyl 2-bromo-4-trifluoromethyl-5-thiazolecarboxylate | 98 | 40 | 43 | 68 |
| Alachlor | 4.48 | Ethyl 2-bromo-4-trifluoromethyl-5-thiazolecarboxylate | 98 | 75 | 65 | 68 |
| Alachlor | — | Ethyl 2-iodo-4-trifluoromethyl-5-thiazolecarboxylate | 0 | 0 | 15 | 60 |
| Alachlor | 0.28 | Ethyl 2-iodo-4-trifluoromethyl-5-thiazolecarboxylate | 85 | 20 | 30 | 73 |
| Alachlor | 1.12 | Ethyl 2-iodo-4-trifluoromethyl-5-thiazolecarboxylate | 98 | 45 | 45 | 80 |
| Alachlor | 4.48 | Ethyl 2-iodo-4-trifluoromethyl-6-thiozolecarboxylate | 98 | 80 | 63 | 85 |
| Alachlor | — | p-Chlorophenyl 2-chloro-4-trifluoromethyl-5-thiazolecarboxylate | 0 | 0 | 0 | 0 |
| Alachlor | 0.28 | p-Chlorophenyl 2-chloro-4-trifluoromethyl-5-thiazolecarboxylate | 60 | 0 | 0 | 5 |
| Alachlor | 1.12 | p-Chlorophenyl 2-chloro-4-trifluoromethyl-5-thiazolecarboxylate | 90 | 15 | 10 | 13 |
| Alachlor | 4.48 | p-Chlorophenyl 2-chloro-4-trifluoromethyl-5-thiazolecarboxylate | 99 | 78 | 45 | 25 |
| Alachlor | — | Butoxyethyl 2-chloro-4-trifluoromethyl-5-thiazolecarboxylate | 0 | 0 | 0 | 5 |
| Alachlor | 0.28 | Butoxyethyl 2-chloro-4-trifluoromethyl-5-thiazolecarboxylate | 83 | 10 | 10 | 18 |
| Alachlor | 1.12 | Butoxyethyl 2-chloro-4-trifluoromethyl-5-thiazolecarboxylate | 93 | 48 | 40 | 50 |
| Alachlor | 4.48 | Butoxyethyl 2-chloro-4-trifluoromethyl-5-Thiazolecarboxylate | 99 | 70 | 60 | 45 |

As noted, selected weed species were planted as a control to determine the efficiency of the herbicide. At rates between 0.28 and 1.12 kilograms per hectare, weed inhibition ranged from 80 to 100 percent.

EXAMPLE 9

A good grade of top soil is placed in a container and compacted to a depth of approximately 1.27 cm. from the top of said container. A predetermined number of sorghum, rice, corn, barnyard grass and foxtail seeds are applied to the soil surface. The seeds are then covered with top soil that had been treated with the herbicide and safening agent by applying said herbicide and safening agent to the soil and incorporating the herbicide and safening agent therein. The plants are observed at the end of approximately 19 days and the results in terms of percent inhibition recorded. Table XVII summarizes the results of tests conducted in accordance with Example 9.

Table XVII

| Herbicide | Rate (kg/h) | Safening Agent | Rate (kg/h) | Percent Inhibition | | | | |
|---|---|---|---|---|---|---|---|---|
| | | | | Rice | Sorghum | Corn | Barnyard Grass | Foxtail |
| N-(ethoxymethyl)-N-(2-ethyl-6-methyl-1-cyclohexen-1-yl)-2-chloroacetamide | 0.28 | — | — | 80 | 63 | 35 | 99 | 99 |
| | 2.24 | | | 100 | 98 | 94 | 100 | 100 |
| N-(ethoxymethyl)-N-(2-ethyl-6-methyl-1-cyclo- | 0.28 | Ethyl 2-chloro-4-trifluoromethyl-5-thiazolecarboxylate | 8.96 | 65 | 8 | 0 | 99 | 99 |
| | 2.24 | | 8.96 | 98 | 53 | 20 | 100 | 100 |

Table XVII-continued

| Herbicide | Rate (kg/h) | Safening Agent | Rate (kg/h) | Percent Inhibition | | | | |
|---|---|---|---|---|---|---|---|---|
| | | | | Rice | Sorghum | Corn | Barnyard Grass | Foxtail |
| hexen-1-yl)-2-chloroacet-amide | | | | | | | | |
| N-(ethoxy-methyl)-N-(2,5-dimethyl-1-cyclopenten-1-yl)-2-chloro-acetamide | 0.28 | — | — | 35 | 18 | 10 | 99 | 99 |
| | 2.24 | — | — | 98 | 40 | 35 | 100 | 100 |
| N-(ethoxy-methyl)-N-(2,5-dimethyl-1-cyclopenten-1-yl)-2-chloro-acetamide | 0.28 | Ethyl 2-chloro-4-trifluoromethyl-5-thiazolecarboxylate | 8.96 | 30 | 0 | 0 | 99 | 99 |
| | 2.24 | | 8.96 | 85 | 15 | 10 | 99 | 99 |

EXAMPLE 10

Two rows of each crop and weed were seeded at 1.86 to 3.1 cm. depth in Ray slit loam soil. The soil is then treated with the herbicide and safening agent. Approximately 19 days later, the plants were observed and the results recorded. Table XVIII summarizes the results of tests conducted in accordance with Example 10.

Table XVIII

| Herbicide | Rate (kg/h) | Safening Agent | Rate (kg/h) | Percent Inhibition | | | | | | | |
|---|---|---|---|---|---|---|---|---|---|---|---|
| | | | | Corn | Sorghum | Rice | Jimson weed | Morning Glory | Barnyard Grass | Panicum | Foxtail |
| Alachlor | 4.48 | — | — | 28 | 77 | 100 | 89 | 52 | 100 | 100 | 100 |
| Alachlor | 4.48 | Ethyl 2-trifluoromethyl-5-thiazolecarboxylate | 2.24 | 13 | 33 | 100 | 93 | 60 | 100 | 100 | 100 |
| 2-Chloro-N-(2-methoxy-1-methyl-ethyl)-6'-ethyl-o-aceto-toluidide | 4.48 | — | — | 62 | 87 | 100 | 92 | 42 | 100 | 100 | 100 |
| | 4.48 | Ethyl 2-chloro-4-trifluoromethyl-5-thiazolecarboxylate | 2.24 | 23 | 28 | 100 | 90 | 40 | 100 | 100 | 100 |
| 2-Chloro-N-(ethoxymethyl)-6'-ethyl-o-aceto-toluidide | 3.36 | — | — | 60 | 89 | 100 | 99 | 65 | 100 | 100 | 100 |
| | 3.36 | Ethyl 2-chloro-4-trifluoromethyl-5-thiazolecarboxylate | 2.24 | 32 | 63 | 100 | 99 | 70 | 100 | 100 | 100 |

The above examples illustrate that the thiazolecarboxylates of the present invention are useful in reducing herbicidal injury to crop plants, especially sorghum and rice. The safening agents may be applied to the plant locus as a mixture, i.e., a mixture of a herbicidally effective amount of acetamide herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weeds to be inhibited, herbicide used, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, small amounts of safening agent are required to treat such seeds. Table XVI illustrates that a weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the compound preferably is formulated as a powder or an emulsifiable concentrate which can be diluted with water by the seed treater for use in the seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkalicasein compositions, long chain alcohols usually containing 10–18 carbon atoms, and condensation products of ethylene oxide with fatty acids, alkylphenols and mercaptans.

PREPARATION OF THE SAFENING AGENTS

The 2,4-disubstituted-5-thiazolecarboxylic acids and derivatives of the foregoing formula may be prepared generally utilizing one of two procedures. The first method encompasses the preparation of 2-oxo-2,3-dihydro-4-substituted-5-thiazolecarboxylates by reacting portions of β-aminoacrylates and chlorocarbonylsulfenyl chloride. Crystallization of the resulting mixture from hexane yields the appropriate 2-oxo-2,3-dihydro-4-substituted-5-thiazolecarboxylate which may be converted to the appropriate 2-chloro-4-substituted-5-thiazolecarboxylate by reaction with excess phosphorus oxychloride. Excess phosphorus oxychloride is removed under reduced pressure and the residue poured into ice water. Extraction with ether and washing with 5% sodium hydroxide results in the 2-chloro-4-substituted-5-thiazolecarboxylate. For purposes of clarification, this method is summarized by the following scheme:

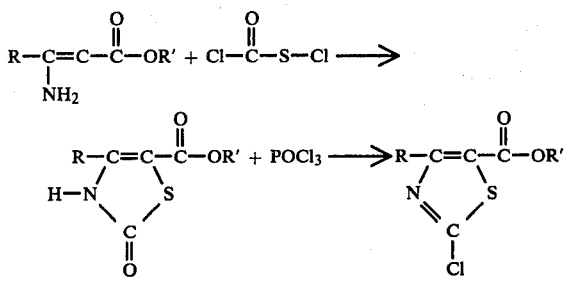

β-aminoacrylates may be prepared according to known procedures such as that specified in Lutz et al, *Journal of Heterocyclic Chemistry*, Volume 9, Page 513 (1972) or they may be prepared by mixing 0.5 moles of ethyl acetoacetate or methyl acetoacetate in 200 ml. of methanol and 100 ml. of saturated sodium acetate and passing through the appropriate nitrile (perfluorinated if R is to be perfluorinated) for several hours. The reaction mixture is poured into ice water and the organic layer extracted with ether. The ether solution is dried and concentrated and the residue is distilled. A mixture of about 0.1 mole of said residue and 50 ml. of 30% ammonium hydroxide or sodium hydroxide is stirred for a long period. The reaction mixture is extracted with methylene chloride and the methylene chloride extracts dried and concentrated. Fractional distillation of the residue results in the β-aminoacrylate.

In order to more fully illustrate the manner in which the 2,4-disubstituted-5-thiazolecarboxylates of the present invention are prepared, the following examples are presented.

EXAMPLE 11

Preparation of Ethyl 2-Chloro-4-Trifluoromethyl-5-Thiazolecarboxylate.

A mixture of 13.0 g (0.0992 mole) of chlorocarbonylsulfenyl chloride, 17 g (0.0928 mole) of ethyl 3-amino-4,4,4-trifluorocrotonate and 50 ml. of chlorobenzene was heated at 135° C. for 2 hours, cooled and triturated with 200 ml. of petroleum ether. The light yellow precipitate was recrystallized from hexane-ether to give 12.2 g (55%) of white prisms, m.p. 121°–123° C., which was identified as ethyl 2,3-dihydro-2-oxo-4-trifluoromethyl-5-thiazolecarboxylate. A mixture of 10 g (0.0415 mole) of ethyl 2,3-dihydro-2-oxo-4-trifluoromethyl-5-thiazolecarboxylate, 30 ml. of POCl$_3$ and 1 ml. of dimethylformamide was held at reflux for 87 hours. The reaction mixture was poured into 500 ml. of ice water and extracted three times with 60 ml. of ether. The ether solution was washed with saturated sodium chloride solution, dried (MgSO$_4$) and concentrated under reduced pressure to give 10.2 g of light yellow solid, m.p. 57°–60° C., which was recrystallized from hexane to give 9.95 g (92.4%) of ethyl 2-chloro-4-trifluoromethyl-5-thiazolecarboxylate as light yellow solid, m.p. 58°–59° C.

Anal. Calc'd. for C$_7$H$_5$F$_3$ClNO$_2$S: C, 32.38; H, 1.94; N, 5.40. Found: C, 32.33; H, 1.98; N, 5.35.

EXAMPLE 12

Preparation of Ethyl 2-Chloro-4-Pentafluoroethyl-5-Thiazolecarboxylate.

To a stirred mixture of 65 g (0.4995) mole of ethyl acetoacetate, 200 ml. of methanol and 100 ml. of saturated sodium acetate at 50° C. was introduced 100 g (0.769 mole) of pentafluoropropionitrile in 3 hours. The reaction mixture was poured into 1200 ml. of water. An oil separated from the reaction mixture. The aqueous solution was extracted with ether. The ether solution was combined with the oil, dried (MgSO$_4$) and concentrated under reduced pressure. The residue was distilled to give 40 g (37%) of ethyl 2-acetyl-3-amino-4,4,5,5,5-pentafluoro-2-pentenoate. A mixture of 21.8 g (0.0790 mole) of ethyl 2-acetyl-3-amino-4,4,5,5,5-pentafluoro-2-pentenoate and 75 ml. of 58% ammonium hydroxide was stirred for 66 hours. The reaction mixture was extracted with ether. The ether solution was dried (MgSO$_4$) and concentrated under reduced pressure. The residue was distilled to give 16.3 g (88%) of ethyl 3-amino-4,4,5,5,5-pentafluoro-2-pentenoate, $n_D^{25}=1.4011$. A well stirred mixture of 54 g (0.23 mole) of ethyl 3-amino-4,4,5,5,5-pentafluoro-2-pentenoate and 31 g (0.237 mole) of chlorocarbonylsulfenyl chloride was held at 100° C. for 1 hour. The reaction mixture was cooled and triturated with hexane. The solid precipitate was washed with water and recrystallized from hexane-ether to give 31 g (46%) of ethyl 2,3-dihydro-2-oxo-4-pentafluoroethyl-5-thiazolecarboxylate, m.p. 95°–97° C. A mixture of 10 g (0.0344 mole) of ethyl 2,3-dihydro-2-oxo-4-pentafluoroethyl-5-thiazole-carboxylate, 4 g (0.0506 mole) of pyridine and 150 ml. of phosphorus oxychloride was held at reflux for 18 hours. Excess phosphorus oxychloride was removed under reduced pressure. The residue was treated with water and extracted with ether. The ether solution was dried (MgSO$_4$) and concentrated under reduced pressure. The residue was distilled to give 7.5 g (71%) of ethyl 2-chloro-4-pentafluoroethyl-5-thiazolecarboxylate, $n_D^{25}=1.4460$.

Anal. Calc'd. for C$_8$H$_5$ClF$_5$NO$_2$S: C, 31.03; H, 1.63; N, 4.52. Found: C, 30.62; H, 1.18; N, 5.08.

EXAMPLE 13

Preparation of Methyl 2-Chloro-4-Heptafluoropropyl-5-Thiazolecarboxylate.

The procedure of Example 12 was repeated utilizing methyl acetoacetate in lieu of ethyl acetoacetate and heptafluorobutyronitrile in lieu of pentafluoropropionitrile to prepare 0.3 g of methyl 2-chloro-4-heptafluoropropyl-5-thiazolecarboxylate as a colorless liquid; $n_D^{25}=1.4352$.

Anal. Calc'd. for C$_8$H$_3$ClF$_7$NO$_2$S: C, 27.80; H, 0.87; N, 4.05. Found: C, 27.42; H, 0.87; N, 4.03.

EXAMPLE 14

Preparation of Ethyl 2-Chloro-4-Trichloromethyl-5-Thiazolecarboxylate.

To 130.14 g (1.00 mole) of ethyl acetoacetate was added 1.5 g of sodium. The reaction temperature increased spontaneously to 50° C. The reaction mixture was cooled with an ice bath. To the cooled reaction mixture was added, with vigorous stirring at 30°–50° C., 144.3 g (1.00 mole) of trichloroacetonitrile in 30 minutes. After complete addition of the trichloroacetonitrile, the reaction mixture was cooled with a dry ice bath. No precipitate of the ethyl 2-acetyl-3-amino-4,4,4-trichlorocrotonate formed. Part of the above product was stirred with 100 ml. of concentrated 28–30% ammonium hydroxide for 2 hours. The reaction mixture was then extracted with ether. The ether solution was dried (CaSO$_4$) and concentrated to give 180 g (82.5%) of crude ethyl 3-amino-4,4,4-trichlorocrotonate. Part of this crude material (20 g) was distilled at 0.5 mm Hg to give 11.7 g of pure product, m.p. 91°–95° C. To a cold (10° C.) solution of 21.8 g (0.0937 mole) of crude ethyl 3-amino-4,4,4-trichlorocrotonate in 15 ml. of chlorobenzene was added 13.5 g (0.103 mole) of chlorocarbonylsulfenyl chloride. The reaction temperature rose spontaneously to 35° C. after the ice water bath was removed. The reaction mixture was stirred at 65° C. for 1 hour, cooled and triturated with petroleum ether to give 10.3 g (38%) of ethyl 2,3-dihydro-2-oxo-4-trichloromethyl-5-thiazolecarboxylate, m.p. 109°–110° C. A mixture of 14.5 g (0.05 mole) of ethyl 2,3-dihydro-2-oxo-4-trichloromethyl-5-thiazolecarboxylate, 10.4 g (0.05 mole) of phosphorus pentachloride, and 100 ml. of phosphorus oxychloride was held at reflux for 7 days. Excess phosphorus oxychloride was removed under reduced pressure. The residue was treated with ice water and the aqueous mixture was extracted with ether. The ether solution was extracted with 10% sodium hydroxide, dried (CaSO$_4$) and concentrated under reduced pressure to give 3.2 g of oil which was chromatographed on silica gel using 5% ethyl acetate-petroleum ether as eluant. The first 1.2 l. of eluant gave 2.27 g of solid which was recrystallized from petroleum ether at low temperature to give 2.13 g (13.8%) of ethyl 2-chloro-4-trichloromethyl-5-thiazolecarboxylate, m.p. 42.5°–43.5° C.

Anal. Calc'd. for C$_7$H$_5$Cl$_4$NO$_2$S: C, 27.18; H, 1.62; N, 4.53; Cl, 45.86. Found: C, 27.27; H, 1.66; N, 4.53; Cl, 45.89.

Various esters may be prepared by reacting the compound of Example 11 with sodium hydroxide to form the free acid and then forming the acid chloride by reaction with thionyl chloride. Reaction of the acid chloride with an alcohol results in the desired ester.

EXAMPLE 15

Preparation of 2-Chloro-4-Trifluoromethyl-5-Thiazolecarboxylic Acid.

A mixture of 116 g (0.4468 mole) of ethyl 2-chloro-4-trifluoromethyl-5-thiazolecarboxylate, 18 g (0.45 mole)

of sodium hydroxide, 200 ml. of water, 400 ml. of tetrahydrofuran was stirred at room temperature for 16 hours and made acidic with 50 ml. of concentrated hydrochloric acid. The reaction mixture was extracted twice with 200 ml. of ether. The ether-tetrahydrofuran solution was dried (MgSO$_4$) and concentrated under reduced pressure. The residual oil was treated with benzene and the benzene solution was concentrated under reduced pressure to remove the last trace of water. The residual solid was recrystallized from hexane-benzene to give 76 g (73.4%) of 2-chloro-4-trifluoromethyl-5-thiazolecarboxylic acid, m.p. 131°-131.5° C.

Anal. Calc'd. for $C_5H_1ClF_3NO_2S$: C, 25.92; H, 0.47; Cl, 15.31; N, 6.05. Found: C, 26.07; H, 0.52; Cl, 15.64; N, 6.10.

EXAMPLE 16

Preparation of 2-Chloro-4-Trifluoromethyl-5-Thiazolecarboxylic Acid Chloride.

A mixture of 36.0 g (0.1554 mole) of the acid of Example 15 and 171 g (1.437 mole) of thionyl chloride were held at reflux for 6 hours. Excess thionyl chloride was removed under reduced pressure and the residue (38.1 g, 98%) was reacted as described in Examples 17-29.

EXAMPLE 17

Preparation of Isopropyl 2-Chloro-4-Trifluoromethyl-5-Thiazolecarboxylate.

The acid chloride of Example 16 (5.2 g), and 10 g of isopropanol were held at reflux for 16 hours. Excess alcohol was removed under reduced pressure. The residue was dissolved in 50 ml. of ether. The ether solution was washed with sodium bicarbonate, dried (MgSO$_4$) and concentrated under reduced pressure. The crude product was distilled at 1 mm. on a Kugelrohr to give 4.9 g (86%) of the desired product as colorless liquid, $n_D^{25} = 1.4655$.

Anal. Calc'd. for $C_8H_7ClF_3NO_2S$: C, 35.10; H, 2.58; N, 5.12; Cl, 12.96. Found: C, 35.15; H, 2.62; N, 5.11; Cl, 12.90.

EXAMPLE 18

Preparation of Benzyl 2-Chloro-4-Trifluoromethyl-5-Thiazolecarboxylate.

The procedure of Example 17 was repeated utilizing benzyl alcohol in lieu of isopropanol to give 2.85 g of a white solid, m.p. 56°-58° C.

Anal. Calc'd. for $C_{12}H_7ClF_3NO_2S$: C, 44.80; H, 2.19; N, 4.35; Cl, 11.02. Found: C, 44.86; H, 2.19; N, 4.34; Cl, 11.09.

EXAMPLES 19-29

Utilizing the appropriate alcohol and the procedure of Example 17, the following compounds have been prepared.

2,2,2-Trichloroethyl 2-Chloro-4-Trifluoromethyl-5-Thiazolecarboxylate, $n_D^{25} = 1.5094$.

Anal. Calc'd. for $C_7H_7Cl_4F_3NO_2S$: C, 23.16; H, 0.56; N, 3.86; Cl, 38.95. Found: C, 23.24; H, 0.62; N, 3.92; Cl, 38.96.

2-Butoxyethyl 2-Chloro-4-Trifluoromethyl-5-Thiazolecarboxylate, $n_D^{25} = 1.4683$.

Anal. Calc'd. for $C_{11}H_{13}ClF_3NO_2S$: C, 39.82; H, 3.95; N, 4.22; Cl, 10.68. Found: C, 40.07; H, 3.87; N, 4.22; Cl, 11,53.

2-Chloroethyl 2-Chloro-4-Trifluoromethyl-5-Thiazolecarboxylate, $n_D^{25} = 1.4965$.

Anal. Calc'd. for $C_7H_4Cl_2F_3NO_2S$: C, 28.59; H, 1.37; N, 4.76; Cl, 24.11. Found: C, 28.67; H, 1.40; N, 4.76; Cl, 24.06.

n-Butyl 2-Chloro-4-Trifluoromethyl-5-Thiazolecarboxylate, $n_D^{25} = 1.4685$.

Anal. Calc'd. for $C_9H_9ClF_3NO_2S$: C, 37.57; H, 3.15; N, 4.87. Found: C, 37.54; H, 3.17; N, 4.90.

n-Hexyl 2-Chloro-4-Trifluoromethyl-5-Thiazolecarboxylate, $n_D^{25} = 1.4657$.

Anal. Calc'd. for $C_{11}H_{13}ClF_3NO_2S$: C, 41.84; H, 4.15; N, 4.44. Found: C, 41.86; H, 4.15; N, 4.43.

n-Octyl 2-Chloro-4-Trifluoromethyl-5-Thiazolecarboxylate, $n_D^{25} = 1.4658$.

Anal. Calc'd. for $C_{13}H_{17}ClF_3NO_2S$: C, 45.42; H, 4.98; N, 4.07. Found: C, 45.58; H, 5.05; N, 4.04.

Phenyl 2-Chloro-4-Trifluoromethyl-5-Thiazolecarboxylate, $n_D^{25} = 1.5389$.

Anal. Calc'd. for $C_{11}H_5ClF_3NO_2S$: C, 42.94; H, 1.64; N, 4.55. Found: C, 42.97; H, 1.67; N, 4.58.

p-Chlorophenyl 2-Chloro-4-Trifluoromethyl-5-Thiazolecarboxylate, $n_D^{25} = 1.5552$.

Anal. Calc'd. for $C_{11}H_4Cl_2F_3NO_2S$: C, 38.60; H, 1.17; N, 4.09. Found: C, 39.08; H, 1.00. N, 4.09.

Allyl 2-Chloro-4-Trifluoromethyl-5-Thiazolecarboxylate, b.p. 68° C. at 0.1 mm; $n_D^{25} = 1.4816$.

Anal. Calc'd. for $C_8H_5ClF_3NO_2S$: C, 35.37; H, 1.86; N, 5.16. Found: C, 35.50; H, 1.93; N, 5.22.

Methyl 2-Chloro-4-Trifluoromethyl-5-Thiazolecarboxylate. The residue was crystallized at low temperature from hexane to give 3.25 g (95%) of methyl 2-chloro-4-trifluoromethyl-5-thiazolecarboxylate as light yellow prisms, m.p. 32°-34° C.

Anal. Calc'd. for $C_6H_3F_3NO_3S$: C, 31.72; H, 1.77; N, 6.17. Found: C, 31.88; H, 1.80; N, 6.20.

Propargyl 2-Chloro-4-Trifluoromethyl-5-Thiazolecarboxylate.

A mixture of 4.63 g (0.02 mole) of 2-chloro-4-trifluoromethyl-5-thiazolecarboxylic acid, 2.42 g (0.02 mole) of propargyl bromide, 2.59 g (0.02 mole) of diisopropylamine, and 50 ml. of methylene chloride was stirred for 16 hours. The methylene chloride solution was washed successively with diluted hydrochloric acid and saturated sodium bicarbonate, dried (MgSO$_4$) and concentrated under reduced pressure. The residue was Kugelrohr distilled to give propargyl 2-chloro-4-trifluoromethyl-5-thiazolecarboxylate as a colorless liquid.

Anal. Calc'd. for $C_8H_3ClF_3NO_2S$: C, 35.63; H, 1.12. Found: C, 35.59; H, 1.29.

The 2,4-disubstituted-5-thiazolecarboxylates of the invention may also be prepared in accordance with the following reaction scheme:

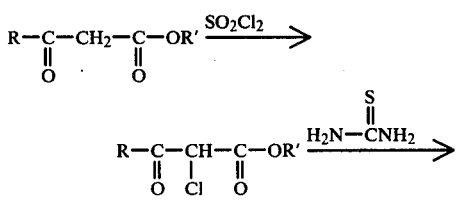

-continued

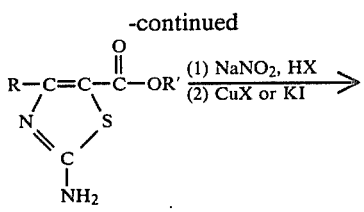

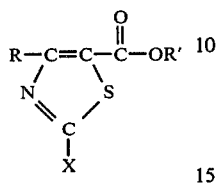

In accordance with the above reaction scheme, ketoesters in chloroform are added dropwise to one equivalent of sulfuryl chloride. The reaction mixture is held at reflux for a number of hours and the chloroform removed under reduced pressure. An equimolar portion of the resultant 2-chloro-3-ketoester is added to thiourea in ethanol and held at reflux for 16–20 hours. Ethanol is then removed under reduced pressure and the residue neutralized with sodium bicarbonate solution to give a 2-amino-4-alkyl-5-thiazolecarboxylic acid ester. A solution of said ester in concentrated acid is diazotized at $-5°$ to $30°$ C. with sodium nitrite. The resulting diazonium salt solution is poured into the corresponding cuprous halide or potassium iodide solution. After gas evolution has subsided, the reaction mixture is extracted with ether. The ether extract is dried and concentrated and the residue is purified by either Kugelrohr distillation at reduced pressure or by chromatography.

EXAMPLE 30

Preparation of Ethyl 2-Chloro-4-Ethyl-5-Thiazolecarboxylate

Ethyl 2-chloro-3-oxo-pentanoate is prepared from ethyl 3-oxo-pentanoate and sulfuryl chloride utilizing the procedure of Bankowski et al, *Rocz. Chem.*, Volume 49, Page 1899 (1971). A mixture of 9.2 g (0.0515 mole) of ethyl 2-chloro-3-oxo-pentanoate, 3.92 g (0.0515 mole) of thiourea and 30 ml. of ethanol was held at reflux for 17 hours. Ethanol was removed under reduced pressure and the residue was treated with 300 ml. of saturated sodium bicarbonate solution. The solid precipitate was collected to give 11.2 g of white solid, m.p. 165°–170° C. which was recrystallized from ethanol to give 7.7 g (75%) of ethyl 2-amino-4-ethyl-5-thiazolecarboxylate as colorless prisms, m.p. 177°–179° C. To a solution of 7.0 g (0.0349 mole) of ethyl 2-amino-4-ethyl-5-thiazolecarboxylate and 0.2 g of $CaSO_4$ in 60 ml. of concentrated HCl was added dropwise a solution of $NaNO_2$ in 20 ml. of water in such a way that the reaction temperature did not exceed 30° C. The reaction mixture was stirred for 30 minutes and poured into a solution of 3.5 g (0.035 mole) of cuprous chloride in 30 ml. of 6 N HCl. The resulting dark blue solution was stirred for 30 minutes and extracted with ether. The ether solution was dried and concentrated under reduced pressure. The residue was Kugelrohr distilled at 2 mm. to give 4.35 g of yellow liquid which was chromatographed on silica gel to give 4.0 g (52%) of the desired product as colorless liquid, $n_D^{25} = 1.5189$.

Anal. Calc'd. for $C_8H_{10}ClNO_2S$: C, 43.73; H, 4.59; N, 6.38. Found: C, 43.88; H, 4.62; N, 6.34.

EXAMPLE 31

Preparation of Ethyl 2-Chloro-4-Isopropyl-5-Thiazolecarboxylate.

Ethyl 2-chloro-4-methyl-3-oxo-pentanoate is prepared in accordance with the literature procedure discussed in Example 30. A mixture of 15.0 g (0.0799 mole) of ethyl 2-chloro-4-methyl-3-oxo-pentanoate, 61 g (0.0802 mole) of thiourea and 60 ml. of ethanol was held at reflux for 21 hours. Ethanol was removed under reduced pressure and the residual oil was treated with 400 ml. of saturated sodium bicarbonate solution. The precipitate was collected to give 14.9 g of white solid, m.p. 172°–174° C., which was recrystallized from ethanol-water to give 13.6 g (82%) of ethyl 2-amino-4-isopropyl-5-thiazolecarboxylate as white prisms, m.p. 174°–178° C. A solution of 2.14 g (0.010 mole) of ethyl 2-amino-4-isopropyl-5-thiazolecarboxylate and 0.1 g of $CaSO_4$ in 40 ml. of concentrated hydrochloric acid was cooled with an ice bath. When the temperature of the reaction solution dropped below 10° C., the hydrochloride salt precipitated out of solution. The reaction mixture was allowed to warm to room temperature and the hydrochloride salt gradually dissolved again. To the above solution was added dropwise 1.0 g (0.0144 mole) of $NaNO_2$ in 10 ml. of water in 15 minutes. After completion of addition of the $NaNO_2$ solution, the reaction mixture was stirred for another 5 minutes. Cuprous chloride (1.0 g, 0.010 mole) was added to the above solution. A vigorous evolution of gas occurred. The dark blue mixture turned light blue after stirring for 5 minutes. The reaction mixture was extracted twice with 50 ml. of ether. The ether solution was washed successively with water, saturated sodium bicarbonate and saturated NaCl solution, dried ($MgSO_4$) and concentrated under reduced pressure to give 1.8 g of oil which was crystallized from hexane to give 0.05 g of 2,2'-bis-(ethyl 4-isopropyl-5-thiazolecarboxylate) as white needles, m.p. 192°–194° C.

The mother liquor was concentrated under reduced pressure and the residue was chromatographed on a silica gel column with $Et_2O$-petroleum ether as eluant. The first fraction (using 1 l. of 1% ether-petroleum ether as eluant) contained 1.2 g of oil which was distilled on a Kugelrohr at 2 mm. (pot temperature 100°–120° C.) to give 1.15 g (49%) of ethyl 2-chloro-4-isopropyl-5-thiazolecarboxylate as a colorless liquid, $n_D^{25} = 1.5145$.

Anal. Calc'd. for $C_9H_{12}ClNO_2S$: C, 46.24; H, 5.18; N, 5.99. Found: C, 46.40; H, 5.22; N, 6.06.

EXAMPLE 32

Preparation of Ethyl 2-Chloro-4-t-Butyl-5-Thiazolecarboxylate.

Utilizing ethyl 2-chloro-4,4-dimethyl-3-oxo-pentanoate and the procedure of Example 31, ethyl 2-chloro-4-t-butyl-5-thiazolecarboxylate is prepared.

Anal. Calc'd. for $C_{10}H_{14}ClNO_2S$: C, 48.48; H, 5.70; N, 5.56. Found: C, 48.41; H, 5.73; N, 5.62.

EXAMPLE 33

Preparation of Ethyl 2-Iodo-4-Trifluoromethyl-5-Thiazolecarboxylate.

To a cold ($-5°$ C.) solution of 4.0 g (0.0166 mole) of ethyl 2-amino-4-trifluoromethyl-5-thiazolecarboxylate, prepared according to U.S. Pat. No. 2,726,237, in 30 ml.

of 85% phosphoric acid and 30 ml. of 70% nitric acid was added a solution of 1.26 g (0.0166 mole) of sodium nitrite in 10 ml. of water in 10 minutes. The reaction mixture was stirred for 10 minutes and poured into a solution of 10 g of potassium iodide in 100 ml. of water. The reaction mixture was stirred overnight and extracted with ether. The ether solution was dried and concentrated and the residue was chromatographed on silica gel to give 1.5 g of the desired product, m.p. 75°–76° C.

Anal. Calc'd. for $C_7H_5F_3INO_3S$: C, 23.94; H, 1.44; N, 3.99; I, 36.15. Found: C, 23.93; H, 1.44; N, 3.95; I, 36.08.

EXAMPLE 34

Preparation of Ethyl 2-Bromo-4-Trifluoromethyl-5-Thiazolecarboxylate.

To a solution of 4.5 g (0.0187 mole) of ethyl 2-amino-4-trifluoromethyl-5-thiazolecarboxylate in 50 ml. of 85% phosphoric acid at −10° C. was added 25 ml. of nitric acid. To this mixture was added dropwise at −10° C. to −5° C. a solution of 4.0 g (0.0579 mole) of sodium nitrite in 20 ml. of water in 30 minutes. This mixture was stirred for 10 minutes at −10° C. to −5° C. and poured into a solution of 2.70 g (0.0187 mole) of freshly prepared cuprous bromide in 20 ml. of hydrobromic acid. A vigorous evolution of gas occurred. The reaction mixture was stirred for 5 minutes and diluted with water. The solid suspension was filtered and air-dried to give 4.8 g of solid which was chromatographed on silica gel using ether/petroleum ether (1:4) as eluant. The first 1 liter of eluate gave 3.7 g of solid which was recrystallized from petroleum ether to give 2.9 g (51%) of the desired product as white needles, m.p. 75.5°–76.5° C.

Anal. Calc'd. for $C_7H_5BrF_3NO_2S$: C, 27.64; H, 1.66; N, 4.61; Br, 26.28. Found: C, 27.65; H, 1.65; N, 4.61; Br, 26.27.

EXAMPLE 35

Preparation of Ethyl 2-Fluoro-4-Trifluoromethyl-5-Thiazolecarboxylate.

A mixture of 26 g (0.1 mole) of ethyl 2-chloro-4-trifluoromethyl-5-thiazolecarboxylate, 37 g (0.55 mole) of potassium fluoride, and 0.11 g of 1,4,7,10,13,16-hexaoxacyclooctadecane (18-CROWN-6, Aldrich Chemical Company) was held at reflux for 23 hours. Since an analysis showed the reaction to be incomplete, another 45 g (0.77 mole) of potassium fluoride was added and the reaction mixture held at reflux for 64 hours. To said mixture, 0.15 g of 18-CROWN-6 and an additional 27 g (0.40 mole) of potassium was added and held at reflux for 22 hours. Due to poor cooling overnight some of the solvent had evaporated. The reaction mixture was cooled and 300 ml. of acetonitrile added. The acetonitrile was filtered and concentrated. The residue was Kugelrohr distilled to give 13.7 g of a material which was separated by spinning band column at 15 mm Hg to give 4.2 g of the desired product, $n_D^{24} = 1.4348$.

Thiazolecarboxylates of the invention in which X is lower alkoxy or phenoxy or substituted phenoxy may be prepared by reacting the halogenated analogue with sodium alkoxide or phenol in the presence of potassium carbonate.

EXAMPLE 36

Preparation of Ethyl 2-Phenoxy-4-Trifluoromethyl-5-Thiazolecarboxylate.

A mixture of 5.2 g (0.02 mole) of ethyl 2-chloro-4-trifluoromethyl-5-thiazolecarboxylate, 1.88 g (0.02 mole) of phenol, 2.76 g (0.02 mole) of $K_2CO_3$ and 50 ml. of acetone was held at reflux for 3 days. Acetone was removed under reduced pressure. The residue was treated with water, extracted with ether. The ether solution was dried ($MgSO_4$) and concentrated under reduced pressure. The residual solid was heated with hexane, cooled and filtered to give 4.8 g (76%) of the desired product, m.p. 52°–54° C.

Anal. Calc'd. for $C_{13}H_{10}F_3NO_2S$: C, 49.21; H, 3.18; N, 4.41. Found: C, 49.27; H, 3.19; N, 4.38.

EXAMPLE 37

Preparation of Ethyl 2-Ethoxy-4-Triethoxymethyl-5-Thiazolecarboxylate.

To a warm solution of sodium ethoxide prepared from 2.0 g (0.0869 mole) of Na and 50 ml. of ethanol was added 5.2 g (0.02 mole) of ethyl 2-chloro-4-trifluoromethyl-5-thiazolecarboxylate. The mixture was stirred for 4 hours. Ethanol was removed under reduced pressure. The residue was treated with water and extracted with ether. The ether solution was washed with saturated sodium bicarbonate, dried ($MgSO_4$) and concentrated under reduced pressure. The residue was distilled to give 2.2 g of the desired product as an oil, b.p. 115° C. at 0.1 mm; $n_D^{25} = 1.4776$.

Anal. Calc'd. for $C_{15}H_{25}NO_6S$: C, 51.86; H, 7.25; N, 4.03. Found: C, 51.36; H, 7.03; N, 4.57.

EXAMPLE 38

Preparation of Ethyl 2-Ethoxy-4-Trifluoromethyl-5-Thiazolecarboxylate.

To a cold (0° C.) solution of sodium ethoxide, prepared from 0.46 g (0.02 mole) of sodium and 40 ml. of dried ethanol, was added 5.2 g (0.02 mole) of ethyl 2-chloro-4-trifluoromethyl-5-thiazolecarboxylate. A precipitate formed immediately. The reaction mixture was heated to 80° C. and then poured into ice water. The precipitate was collected to give 4.2 g (78%) of the desired product as a white solid, m.p. 30.5°–31.5° C.

Anal. Calc'd. for $C_9H_{10}F_3NO_3S$: C, 40.15; H, 3.74; N, 5.20. Found: C, 40.11; H, 3.75; N, 5.19.

EXAMPLE 39

Preparation of Ethyl 2-(2′,4′-Dichlorophenoxy)-4-Methyl-5-Thiazolecarboxylate.

A mixture of 6.24 g (0.03 mole) of ethyl 2-chloro-4-methyl-5-thiazolecarboxylate, 4.89 g (0.03 mole) of 2,4-dichlorophenol, 4.14 g (0.03 mole) of potassium carbonate and 40 ml. of acetone was held at reflux for 89 hours. Acetone was removed under reduced pressure. The residue was treated with 50 ml. of water and extracted with ether. The ether solution was washed successively with saturated sodium bicarbonate, 30 ml. of 10% sodium hydroxide and 50 ml. of water. The ether solution was dried ($MgSO_4$) and concentrated. The residue was recrystallized from hexane to give 5.8 g (58%) of ethyl 2-(2′,4′-dichlorophenoxy)-4-methyl-5-thiazolecarboxylate as a white solid, m.p. 71°–73° C.

Anal. Calc'd. for $C_{13}H_{11}Cl_2NO_3S$: C, 47.00; H, 3.34; N, 4.22; Cl, 21.34. Found: C, 47.04; H, 3.34; N, 4.21; Cl, 21.36.

Amides are prepared by reacting the appropriate acid chloride with the appropriate amine.

EXAMPLE 40

Preparation of N,N-Diethyl-2-Chloro-4-Trifluoromethyl-5-Thiazolecarboxamide.

To a well-stirred solution of 4.0 g (0.0160 mole) of the acid chloride of Example 16 in 20 ml. of ether was added dropwise 2.34 g (0.032 mole) of diethylamine in 5 ml. of ether. The insoluble salt was filtered. The ether solution was washed with water, dried and concentrated under reduced pressure. The residue was crystallized from hexane at low temperature to give 4.1 g of the desired product, m.p. 40°–41° C.

Anal. Calc'd. for $C_9H_{10}ClF_3N_2OS$: C, 37.70; H, 3.51; N, 9.77; Cl, 12.38. Found: C, 37.66; H, 3.53; N, 9.78; Cl, 12.33.

Salts may be prepared by reaction of the free acid with the appropriate base.

EXAMPLE 41

Preparation of Sodium Salt of 2-Chloro-4-Trifluoromethyl-5-Thiazolecarboxylic Acid, Monohydrate.

A mixture of 116 g (0.4468 mole) of ethyl 2-chloro-4-trifluoromethyl-5-thiazolecarboxylate, 18 g (0.45 mole) of sodium hydroxide, 200 ml. of water and 400 ml. of tetrahydrofuran was stirred at room temperature for 16 hours. The aqueous solution was concentrated and dried under vacuum to give the sodium salt of 2-chloro-4-trifluoromethyl-5-thiazolecarboxylate, monohydrate as a white solid, m.p. 211°–215° C.

Anal. Calc'd. for $C_5H_2ClF_3NO_3S$: C, 22.10; H, 0.74; N, 5.16. Found: C, 22.14; H, 0.71; N, 5.21.

EXAMPLE 42

Preparation of Triethanolamine Salt of 2-Chloro-4-Trifluoromethyl-5-Thiazolecarboxylic Acid.

To a cold (5° C.) solution of 6.93 g (0.03 mole) of 2-chloro-4-trifluoromethyl-5-thiazolecarboxylic acid in 20 ml. of ether was added 4.47 g (0.03 mole) of triethanolamine. The reaction mixture was stirred at room temperature for 18 hours and filtered to give 8.78 g (77%) of the desired product, m.p. 101°–102° C.

Anal. Calc'd. for $C_{11}H_{16}ClF_3N_2O_5S$: C, 34.69; H, 4.23; N, 7.36. Found: C, 34.89; H, 4.07; N, 7.39.

EXAMPLE 43

Preparation of Isopropylamine Salt of 2-Chloro-4-Trifluoromethyl-5-Thiazolecarboxylic Acid.

To a cold (6° C.) solution of 4.55 g (0.0196 mole) of the free acid in 20 ml. of ether was added dropwise a solution of 1.16 g (0.0196 mole) of isopropylamine in 10 ml. of ether. The reaction mixture was stirred at room temperature for 1 hour and the white precipitate was filtered to give 5.50 g (96.5%) of the desired product, m.p. 132°–134° C.

Anal. Calc'd. for $C_8H_{10}ClF_3N_2O_2S$: C, 33.05; H, 3.47; N, 9.64. Found: C, 33.47; H, 3.55; N, 9.72.

EXAMPLE 44

Preparation of Diethylamine Salt of 2-Chloro-4-Trifluoromethyl-5-Thiazolecarboxylic Acid.

To a cold (6° C.) solution of 6.93 g (0.03 mole) of the free acid in 20 ml. of ether was added 2.19 g (0.03 mole) of diethylamine in 100 ml. of ether. The precipitate, which formed immediately, was filtered to give 7.95 g (86.4%) of the desired product, m.p. 131°–132° C.

Anal. Calc'd. for $C_9H_{12}ClF_3N_2O_2S$: C, 35.47; H, 3.97; N, 9.20. Found: C, 35.60; H, 3.97; N, 9.21.

In accordance with the novel aspects of the present invention, the thiazolecarboxylates have been found to be effective in reducing herbicidal injury to selected crop plants due to application of acetamide herbicides. A preferred embodiment are those thiazolecarboxylates substituted in the 4-position with a trifluoromethyl moiety. Such compounds have been found to be quite superior in their ability to reduce herbicidal injury. As illustrated in Table IX, thiazolecarboxylates substituted by a trifluoromethyl in the 4-position are clearly superior to those substituted in the 4-position by methyl in reducing herbicidal injury to sorghum. Another preferred group of thiazolecarboxylates are those substituted in the 2-position with a halogen, especially chloro. Most preferred are those thiazole alkyl esters of the thiazolecarboxylic acid having a chloro in the 2-position and a trifluoromethyl in the 4-position.

While the compounds of the invention generally tend to safen rice and sorghum crops to the herbicidal effects of acetamide herbicides, especially acetanilide herbicides, those skilled in the art will appreciate that the compounds of the invention may be used most effectively in safening sorghum against injury due to alachlor and 2-chloro-N-(2-methoxy-1-methylethyl)-6'-ethyl-o-acetotoluidide, especially alachlor, and rice, especially direct-seeded rice, against the herbicidal effects of butachlor.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

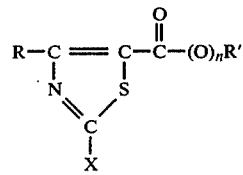

wherein n is zero or one; X is selected from the group consisting of chloro, bromo, iodo, fluoro, lower alkoxy, phenoxy and phenoxy substituted by one or two groups independently selected from the group consisting of lower alkyl and halogen; R is selected from the group consisting of alkyl having up to five carbon atoms wherein at least one hydrogen atom has been replaced by a halogen atom and triethoxymethyl; when n is one, R' is selected from the group consisting of hydrogen, agriculturally acceptable cations, alkyl having from one to ten carbon atoms, lower alkenyl, lower alkynyl, lower alkoxy lower alkyl, alkyl having up to five carbon atoms wherein at least one hydrogen atom has been replaced by a halogen atom, benzyl, phenyl and phenyl substituted by one or two members selected from the group consisting of halogen, lower alkyl, trifluoromethyl and nitro; when n is zero, R' is selected from the group consisting of chloro, amino and mono or di-lower alkyl amino.

2. A compound according to claim 1 wherein n is one.

3. A compound according to claim 1 wherein n is zero.

4. A compound according to claim 2 wherein X is chloro.

5. A compound according to claim 2 wherein R is alkyl having up to five carbon atoms wherein at least one hydrogen atom has been replaced by a halogen atom.

6. A compound according to claim 5 wherein R is trifluoromethyl.

7. A compound according to claim 2 wherein R' is hydrogen, alkyl having from one to ten carbon atoms, lower alkenyl, lower alkynyl, lower alkoxy lower alkyl, alkyl having up to five carbon atoms wherein at least one hydrogen atom has been replaced by a halogen atom, benzyl, phenyl or phenyl substituted by one or two members selected from the group consisting of halogen, lower alkyl, trifluoromethyl and nitro.

8. A compound according to claim 2 wherein R' is hydrogen, alkyl having from one to ten carbon atoms, benzyl, phenyl or phenyl substituted by one member selected from the group consisting of halogen, lower alkyl, trifluoromethyl and nitro.

9. A compound according to claim 2 wherein R' is alkyl having from one to ten carbon atoms.

10. A compound according to claim 2 wherein X is halogen, R is alkyl having up to five carbon atoms wherein at least one hydrogen atom has been replaced by a halogen atom and R' is alkyl having from one to ten carbon atoms.

11. A compound according to claim 10 wherein X is chloro and R is trifluoromethyl.

12. A compound according to claim 2 wherein X is halogen, R is alkyl having up to five carbon atoms wherein at least one hydrogen atom has been replaced by a halogen atom and R' is benzyl.

13. A compound according to claim 12 wherein R is trifluoromethyl.

14. A compound according to claim 2 wherein X is halogen, R is alkyl having up to five carbon atoms wherein at least one hydrogen atom has been replaced by a halogen atom and R' is phenyl or phenyl substituted by halogen.

15. A compound according to claim 1 in which said compound is butyl 2-chloro-4-trifluoromethyl-5-thiazolecarboxylate.

16. A compound according to claim 1 in which said compound is hexyl 2-chloro-4-trifluoromethyl-5-thiazolecarboxylate.

17. A compound according to claim 1 in which said compound is octyl 2-chloro-4-trifluoromethyl-5-thiazolecarboxylate.

18. A compound according to claim 1 in which said compound is ethyl 2-chloro-4-trifluoromethyl-5-thiazolecarboxylate.

19. A compound according to claim 1 in which said compound is phenyl 2-chloro-4-trifluoromethyl-5-thiazolecarboxylate.

20. A compound according to claim 1 in which said compound is p-chlorophenyl 2-chloro-4-trifluoromethyl-5-thiazolecarboxylate.

21. A compound according to claim 1 in which said compound is benzyl 2-chloro-4-trifluoromethyl-5-thiazolecarboxylate.

22. A compound according to claim 1 in which said compound is 2-chloro-4-trifluoromethyl-5-thiazolecarboxylic acid.

23. A compound according to claim 1 in which said compound is the α-methylethanamine salt of 2-chloro-4-trifluoromethyl-5-thiazolecarboxylic acid.

24. A compound according to claim 1 in which said compound is allyl 2-chloro-4-trifluoromethyl-5-thiazolecarboxylate.

25. A compound according to claim 1 in which said compound is methyl 2-chloro-4-trifluoromethyl-5-thiazolecarboxylate.

26. A compound according to claim 1 in which said compound is isopropyl 2-chloro-4-trifluoromethyl-5-thiazolecarboxylate.

27. A compound according to claim 1 in which said compound is butoxyethyl 2-chloro-4-trifluoromethyl-5-thiazolecarboxylate.

28. A compound according to claim 1 in which said compound is β-trichloroethyl 2-chloro-4-trifluoromethyl-5-thiazolecarboxylate.

* * * * *